(12) United States Patent
Rioux et al.

(10) Patent No.: US 7,744,591 B2
(45) Date of Patent: Jun. 29, 2010

(54) FOAM ELECTRODE AND METHOD OF USE THEREOF DURING TISSUE RESECTION

(75) Inventors: Robert F. Rioux, Ashland, MA (US); Paul DiCarlo, Middleboro, MA (US); Arnold Oyola, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 350 days.

(21) Appl. No.: 11/611,729

(22) Filed: Dec. 15, 2006

(65) Prior Publication Data
US 2007/0156127 A1 Jul. 5, 2007

Related U.S. Application Data

(60) Provisional application No. 60/755,713, filed on Dec. 29, 2005.

(51) Int. Cl.
*A61B 18/14* (2006.01)
(52) U.S. Cl. ............... 606/32; 606/45; 606/48; 606/49; 606/50
(58) Field of Classification Search .......... 606/32, 606/45, 51, 41, 1, 48, 49, 50; 128/898
See application file for complete search history.

(56) References Cited

U.S. PATENT DOCUMENTS

| 4,383,529 | A | * | 5/1983 | Webster | 604/20 |
| 4,474,570 | A | * | 10/1984 | Ariura et al. | 604/20 |
| 4,731,049 | A | * | 3/1988 | Parsi | 604/20 |
| 4,764,164 | A | * | 8/1988 | Sasaki | 604/20 |
| 5,264,105 | A | * | 11/1993 | Gregg et al. | 204/403.09 |
| 5,310,404 | A | * | 5/1994 | Gyory et al. | 604/20 |
| 5,362,420 | A | * | 11/1994 | Itoh et al. | 252/500 |

(Continued)

FOREIGN PATENT DOCUMENTS

EP 0 895 756 A1 2/1999

(Continued)

OTHER PUBLICATIONS

PCT International Search Report for PCT/US2006/062155, Applicant: Boston Scientific Scimed, Inc., Form PCT/ISA/210 and 220, dated Jul. 28, 2008 (6 pages).

(Continued)

*Primary Examiner*—Lee S Cohen
(74) *Attorney, Agent, or Firm*—Vista IP Law Group LLP

(57) ABSTRACT

Assemblies and methods are provided for resecting a portion of tissue to be removed (e.g., unhealthy tissue, such as cancerous tissue) from a portion of the tissue to be retained (e.g., healthy tissue) within a patient is provided. An electrically conductive fluid, such as saline, may be absorbed into a hydrophilic electrode. Electrical energy (e.g., radio frequency (RF) energy) is conveyed to or from the hydrophilic electrode while being moved in proximity to the tissue along a resection line, whereby tissue adjacent to the resection line is coagulated. A resection member, such as a blunt resection member or a resection electrode, which may be on the same device as the hydrophilic electrode, is used to separate the tissue along the resection line to resect the tissue portion to be removed from the tissue portion to be retained.

21 Claims, 11 Drawing Sheets

U.S. PATENT DOCUMENTS

| | | | | |
|---|---|---|---|---|
| 5,618,265 | A * | 4/1997 | Myers et al. | 604/20 |
| 5,782,848 | A * | 7/1998 | Lennox | 606/159 |
| 5,830,212 | A * | 11/1998 | Cartmell et al. | 606/35 |
| 5,947,961 | A * | 9/1999 | Netherly | 606/32 |
| 5,961,483 | A * | 10/1999 | Sage et al. | 604/20 |
| 6,006,130 | A * | 12/1999 | Higo et al. | 604/20 |
| 6,032,077 | A * | 2/2000 | Pomeranz | 607/101 |
| 6,056,747 | A * | 5/2000 | Saadat et al. | 606/50 |
| 6,071,281 | A * | 6/2000 | Burnside et al. | 606/41 |
| 6,099,526 | A * | 8/2000 | Whayne et al. | 606/41 |
| 6,123,701 | A * | 9/2000 | Nezhat | 606/33 |
| 6,152,920 | A * | 11/2000 | Thompson et al. | 606/41 |
| 6,214,834 | B1 * | 4/2001 | Jadhav et al. | 514/275 |
| 6,411,853 | B1 * | 6/2002 | Millot et al. | 607/50 |
| 6,470,219 | B1 * | 10/2002 | Edwards et al. | 607/101 |
| 6,494,881 | B1 * | 12/2002 | Bales et al. | 606/45 |
| 7,104,990 | B2 * | 9/2006 | Jenkins et al. | 606/49 |
| 7,160,296 | B2 * | 1/2007 | Pearson et al. | 606/42 |
| 7,191,016 | B2 * | 3/2007 | Marshall et al. | 607/122 |
| 2002/0008956 | A1 * | 1/2002 | Niu | 361/502 |
| 2002/0058903 | A1 * | 5/2002 | Murdock | 604/20 |
| 2002/0087208 | A1 * | 7/2002 | Koblish et al. | 607/113 |
| 2003/0055405 | A1 * | 3/2003 | Keusch et al. | 604/890.1 |
| 2003/0060822 | A1 * | 3/2003 | Schaer et al. | 606/41 |
| 2003/0130658 | A1 | 7/2003 | Goble et al. | |
| 2003/0163178 | A1 * | 8/2003 | Davison et al. | 607/101 |
| 2003/0233089 | A1 * | 12/2003 | Ohyama et al. | 606/46 |
| 2004/0230190 | A1 * | 11/2004 | Dahla et al. | 606/41 |
| 2005/0033278 | A1 | 2/2005 | McClurken et al. | |
| 2006/0009756 | A1 * | 1/2006 | Francischelli et al. | 606/32 |
| 2006/0149341 | A1 * | 7/2006 | Palti | 607/63 |
| 2007/0021743 | A1 * | 1/2007 | Rioux et al. | 606/32 |

FOREIGN PATENT DOCUMENTS

| | | |
|---|---|---|
| EP | 1 323 392 A1 | 7/2003 |
| WO | WO 02/24089 A1 | 3/2002 |

OTHER PUBLICATIONS

PCT Written Opinion of the International Search Authority for PCT/US2006/062155, Applicant: Boston Scientific Scimed, Inc., Form PCT/ISA/237, dated Jul. 28, 2008 (5 pages).

Office Action dated May 19, 2009 in European Application No. 06 850 437.2-1265, Applicant: Boston Scientific Scimed, Inc., (4 pages).

* cited by examiner

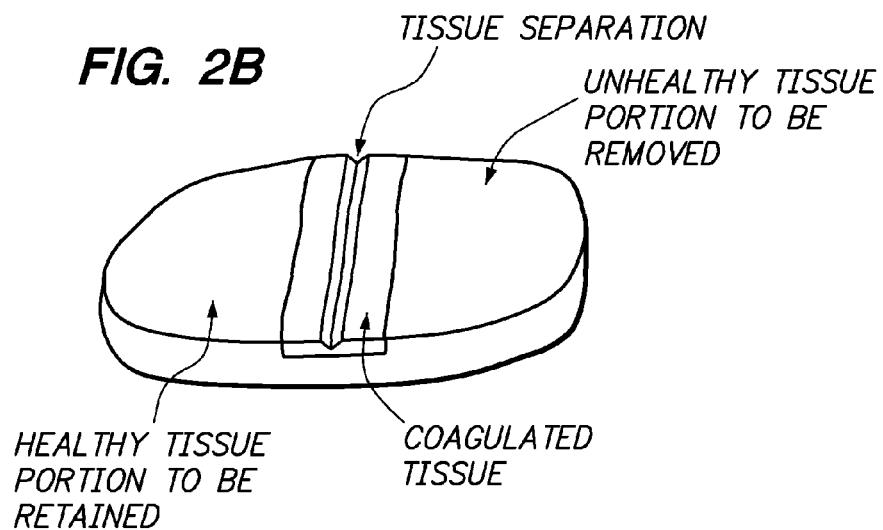
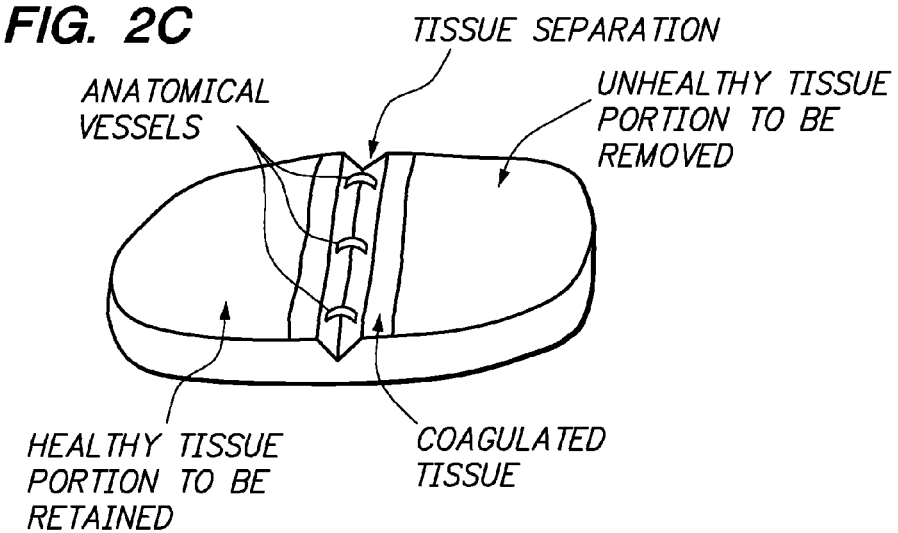
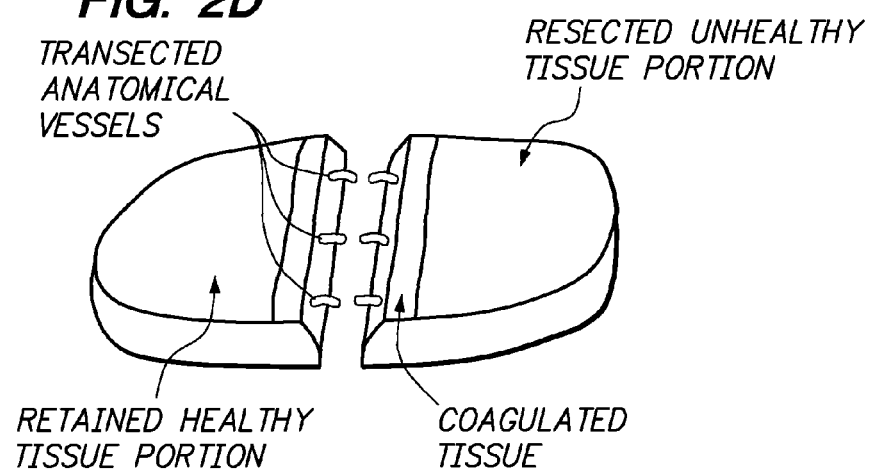

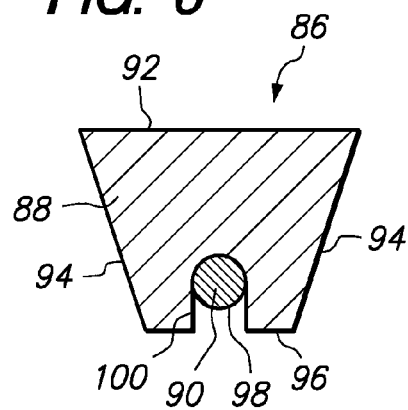
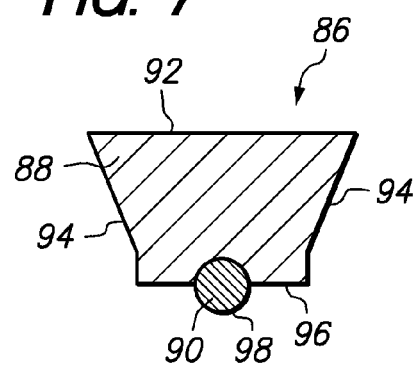
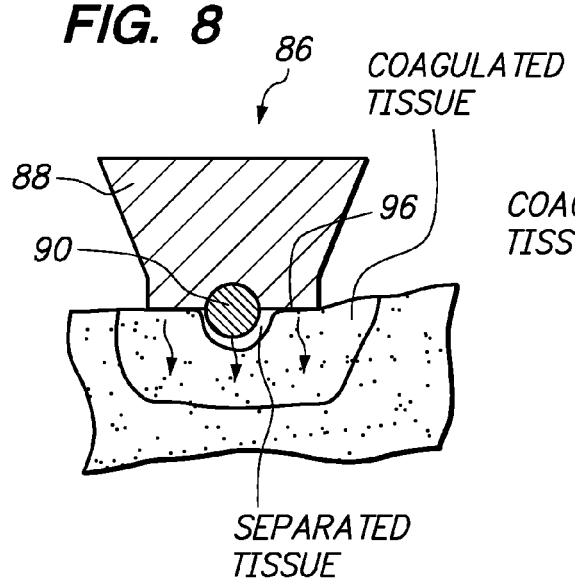
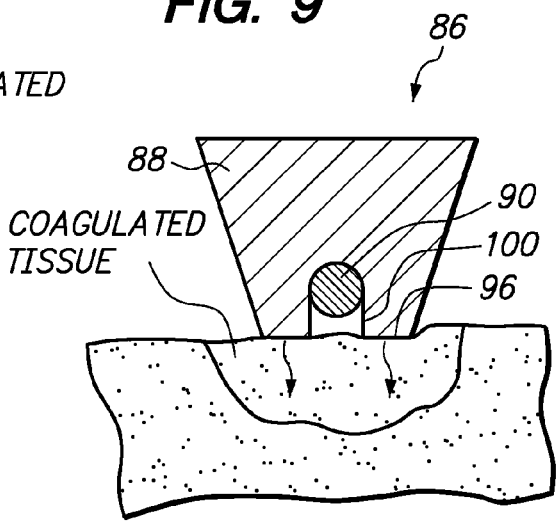

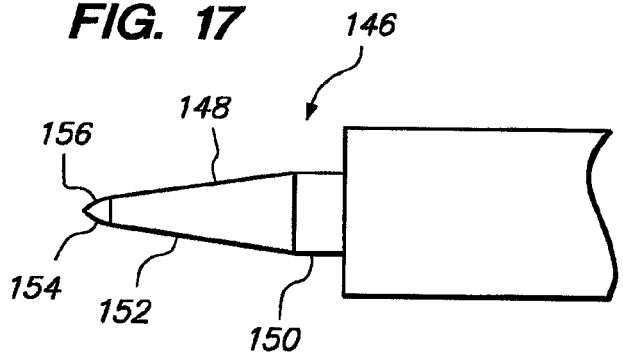
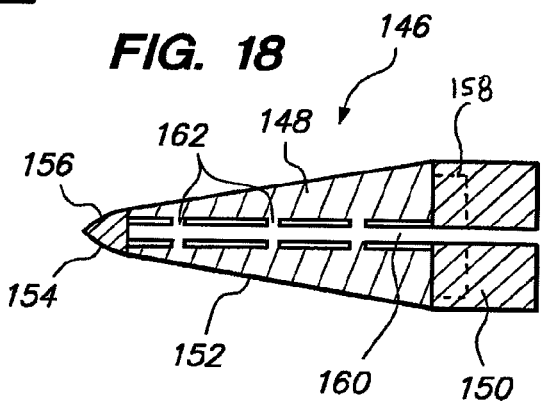
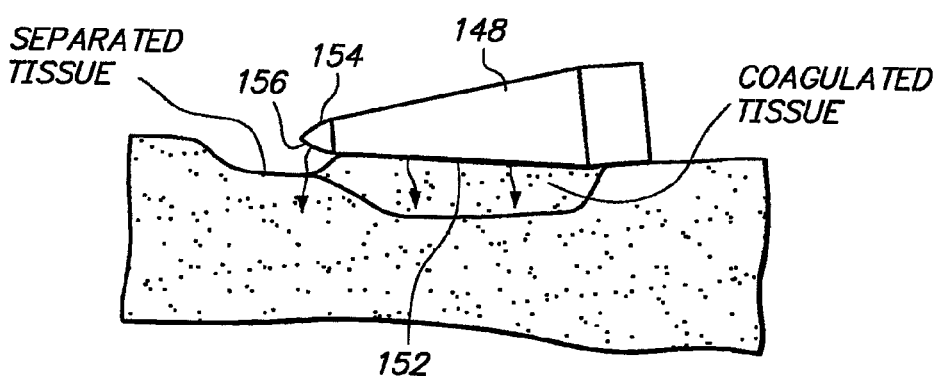
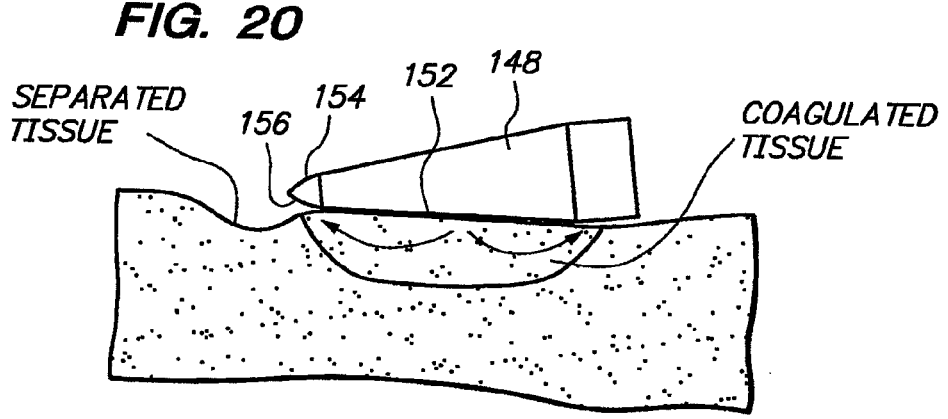

US 7,744,591 B2

FOAM ELECTRODE AND METHOD OF USE THEREOF DURING TISSUE RESECTION

RELATED APPLICATION DATA

The present application claims the benefit under 35 U.S.C. §119 to U.S. provisional patent application Ser. No. 60/755,713 filed Dec. 29, 2005, which is hereby incorporated by reference.

FIELD OF INVENTION

The present inventions generally relate to tissue ablation devices and methods, and particularly to ablation devices and methods for achieving tissue resection.

DESCRIPTION OF RELATED ART

Today, electrosurgery is one of the widely used surgical modalities for treating tissue abnormalities. Electrosurgical devices fall into one of two categories, monopolar devices and bipolar devices. Generally, surgeons are trained in the use of both monopolar and bipolar electrosurgical techniques, and essentially all operating rooms will be found equipped with the somewhat ubiquitous instrumentality for performing electrosurgery.

Monopolar electrosurgical devices typically comprise an electrosurgical probe having a first or "active" electrode extending from one end. The electrosurgical probe is electrically coupled to an electrosurgical generator, which provides a high frequency electric current. A remote control switch is attached to the generator and commonly extends to a foot switch located in proximity to the operating theater. During an operation, a second or "return" electrode, having a much larger surface area than the active electrode, is positioned in contact with the skin of the patient. The surgeon may then bring the active electrode in close proximity to the tissue and activate the foot control switch, which causes electrical current to arc from the distal portion of the active electrode and flow through tissue to the larger return electrode.

For the bipolar modality, no return electrode is used. Instead, a second electrode is closely positioned adjacent to the first electrode, with both electrodes being attached to an electrosurgical probe. As with monopolar devices, the electrosurgical probe is electrically coupled to an electrosurgical generator. When this generator is activated, electrical current arcs from the end of the first electrode to the end of the second electrode, flowing through the intervening tissue. In practice, several electrodes may be employed, and depending on the relative size or locality of the electrodes, one or more electrodes may be active.

Whether arranged in a monopolar or bipolar fashion, the active electrode may be operated to either cut tissue or coagulate tissue. When used to cut tissue, the electrical arcing and corresponding current flow results in a highly intense, but localized heating, sufficient enough to break intercellular bonds, resulting in tissue severance. When used to coagulate tissue, the electrical arcing results in a low level current that denatures cells to a sufficient depth without breaking intercellular bonds, i.e., without cutting the tissue.

Whether tissue is cut or coagulated mainly depends on the geometry of the active electrode and the nature of the electrical energy delivered to the electrode. In general, the smaller the surface area of the electrode in proximity to the tissue, the greater the current density (i.e., the amount of current distributed over an area) of the electrical arc generated by the electrode, and thus the more intense the thermal effect, thereby cutting the tissue. In contrast, the greater the surface area of the electrode in proximity to the tissue, the less the current density of the electrical arc generated by the electrode, thereby coagulating the tissue. Thus, if an electrode having both a broad side and a narrow side is used, e.g., a spatula, the narrow side of the electrode can be placed in proximity to the tissue in order to cut it, whereas the broad side of the electrode can be placed in proximity to the tissue in order to coagulate it. With respect to the characteristics of the electrical energy, as the crest factor (peak voltage divided by root mean squared (RMS)) of the electrical energy increases, the resulting electrical arc generated by the electrode tends to have a tissue coagulation effect. In contrast, as the crest factor of the electrical energy decreases, the resulting electrical arc generated by the electrode tends to have a cutting effect. The crest factor of the electrical energy is typically controlled by controlling the duty cycle of the electrical energy. For example, to accentuate tissue cutting, the electrical energy may be continuously applied to increase its RMS average to decrease the crest factor. In contrast, to accentuate tissue coagulation, the electrical energy may be pulsed (e.g., at a 10 percent duty cycle) to decrease its RMS average to increase the crest factor.

Notably, some electrosurgical generators are capable of being selectively operated in so-called "cutting modes" and "coagulation modes." This, however, does not mean that the active electrode that is connected to such electrosurgical generators will necessarily have a tissue cutting effect if operated in the cutting mode or similarly will have a tissue coagulation effect if operated in the coagulation mode, since the geometry of the electrode is the most significant factor in dictating whether the tissue is cut or coagulated. Thus, if the narrow part of an electrode is placed in proximity to tissue and electrical energy is delivered to the electrode while in a coagulation mode, the tissue may still be cut.

There are many medical procedures in which tissue is cut or carved away for diagnostic or therapeutic reasons. For example, during hepatic transection, one or more lobes of a liver containing abnormal tissue, such as malignant tissue or fibrous tissue caused by cirrhosis, are cut away. There exists various modalities, including mechanical, ultrasonic, and electrical (which includes RF energy), that can be used to effect resection of tissue. Whichever modality is used, extensive bleeding can occur, which can obstruct the surgeon's view and lead to dangerous blood loss levels, requiring transfusion of blood, which increases the complexity, time, and expense of the resection procedure. To prevent extensive bleeding, hemostatic mechanisms, such as blood inflow occlusion, coagulants (e.g., Surgicel™ or Tisseel™), and energy coagulation (e.g., electrosurgical coagulation or argon-beam coagulation), can be used.

In the case where an electrosurgical coagulation means is used, the bleeding can be treated or avoided by coagulating the tissue in the treatment areas with an electro-coagulator that applies a low level current to denature cells to a sufficient depth without breaking intercellular bonds, i.e., without cutting the tissue. Because of their natural coagulation capability, ease of use, and ubiquity, electrosurgical modalities are often used to resect tissue.

During a typical electrosurgical resection procedure, electrical energy can be conveyed from an electrode along a resection line in the tissue. The electrode may be operated in a manner that incises the tissue along the resection line, or coagulates the tissue along the resection line, which can then be subsequently dissected using the same coagulation electrode or a separate tissue dissector to gradually separate the tissue. In the case where an organ is resected, application of RF energy divides the parenchyma, thereby skeletalizing the organ, i.e., leaving vascular tissue that is typically more difficult to cut or dissect relative to the parenchyma.

When a blood vessel is encountered, RF energy can be applied to shrink the collagen in the blood vessel, thereby closing the blood lumen and achieving hemostasis. The blood vessel can then be mechanically transected using a scalpel or scissors without fear of blood loss. In general, for smaller blood vessels less than 3 mm in diameter, hemostasis may be achieved within 10 seconds, whereas for larger blood vessels up to 5 mm in diameter, the time required for hemostasis increases to 15-20 seconds. During or after resection of the tissue, RF energy can be applied to any "bleeders" (i.e., vessels from which blood flows or oozes) to provide complete hemostasis for the resected organ.

When electrosurgically resecting tissue, care must be taken to prevent the heat generated by the electrode from charring the tissue, which generates an undesirable odor, results in tissue becoming stuck on the electrosurgical probe, and most importantly, increases tissue resistance, thereby reducing the efficiency of the procedure. Adding an electrically conductive fluid, such as saline, to the electrosurgery site cools the electrode and keeps the tissue temperature below the water boiling point (100° C.), thereby avoiding smoke and reducing the amount of charring. The electrically conductive fluid can be provided through the probe that carries the active electrode or by another separate device.

Although the application of electrically conductive fluid to the electrosurgery site generally increases the efficiency of the RF energy application, energy applied to an electrode may rapidly diffuse into fluid that has accumulated and into tissue that has already been removed. As a result, if the fluid and removed tissue is not effectively aspirated from the tissue site, the electrosurgery may either be inadequately carried out, or a greater than necessary amount of energy must be applied to the electrode to perform the surgery. Increasing the energy used during electrosurgery increases the chance that adjacent healthy tissues may be damaged. At the same time that fluid accumulation is avoided, care must be taken to ensure that fluid is continuously flowed to the tissue site to ensure that tissue charring does not take place. For example, if flow of the fluid is momentarily stopped, e.g., if the tube supplying the fluid is kinked or stepped on, or the port on the fluid delivery device becomes clogged or otherwise occluded, RF energy may continue to be conveyed from the electrode, thereby resulting in a condition where tissue charring may occur.

While electrosurgical resection of tissue reduces the amount of blood loss, as compared to other tissue resection modalities, it still involves a tedious process that includes painstakingly cutting/dissecting through the parenchyma and ligating and cutting though blood vessels.

There, thus, remains a need to provide a more efficient means for electrosurgically resecting vascularized tissue, while preventing tissue charring and maintaining hemostasis at the treatment site.

SUMMARY OF THE INVENTION

In accordance with a first aspect of the present inventions, a method of resecting a portion of tissue to be removed (e.g., unhealthy tissue, such as cancerous tissue) from a portion of the tissue to be retained (e.g., healthy tissue) within a patient is provided. The tissue can take the form of any tissue requiring treatment, such as an organ, e.g., a liver. The method comprises absorbing an electrically conductive fluid, such as saline, into a hydrophilic electrode. For example, the electrically conductive fluid can be perfused into the hydrophilic electrode under pressure, or the hydrophilic electrode can be dipped into a source of the electrically conductive fluid. The hydrophilic electrode may be composed of an electrically insulative material, in which case, the absorbed electrically conductive solution provides an electrically conductive path through the hydrophilic electrode. The hydrophilic electrode may absorb an amount of the electrically conductive solution equal to at least the dry weight of the hydrophilic electrode, but preferably, absorbs as much electrically conductive solution as possible to maximize the electrical conductivity of the hydrophilic electrode. The method further comprises conveying electrical energy (e.g., radio frequency (RF) energy) to or from the hydrophilic electrode while being moved in proximity to the tissue along a resection line, whereby tissue adjacent to the resection line is coagulated.

Although the present inventions should not necessarily be limited in their broadest aspects, the use of an electrically insulative hydrophilic material is advantageous in that the hydrophilic electrode cannot be activated until it absorbs a sufficient amount of electrically conductive fluid. Thus, unlike other electrosurgical systems that utilize saline, the inactivation of the hydrophilic electrode will prevent tissue charring from occurring if the flow of saline is cutoff or is otherwise insufficient. In addition, because the absorbent nature of the hydrophilic electrode provides only the necessary amount of electrically conductive fluid to the tissue site by limiting the electrically conductive fluid to the tissue-electrode interface, the electrical energy conveyed to or from the hydrophilic electrode is focused at the desired location, and the need for aspirating electrically conductive fluid, which may otherwise accumulate at the tissue site using other saline systems, is obviated.

The method further comprises separating the tissue along the resection line to resect the tissue portion to be removed from the tissue portion to be retained. For example, tissue separation may comprise mechanically or electrically separating the coagulated tissue along the resection line. Thus, it can be appreciated that, because the tissue has been coagulated, blood or fluid loss is prevented, or at least minimized during the resection process. Electrical separation of the tissue may be accomplished with the hydrophilic electrode or another electrode separate from the hydrophilic electrode. In the later case, the hydrophilic electrode and other electrode may be conveniently mounted on a single probe, and/or electrical energy may be conveyed to or from the hydrophilic electrode and the other electrode, wherein tissue coagulation and tissue separation is simultaneously achieved. The tissue coagulation may be performed prior to the tissue separation, whereby the coagulated tissue is separated. Optionally, electrical energy may be conveyed to or from the hydrophilic electrode to seal an anatomical vessel (e.g., a blood vessel) that traverses the resection line, and the sealed blood vessel can then be transected.

In accordance with a second aspect of the present inventions, an electrosurgical probe is provided. The electrosurgical probe comprises an elongated probe shaft, which may be rigid, and a tissue coagulation electrode mounted to the distal end of the probe shaft. The coagulation electrode is configured for absorbing an electrically conductive fluid, and has a leading surface that can be placed in contact with tissue. The leading surface of the coagulation electrode may be straight, such that it can be placed along a straight resection line. The coagulation electrode may be composed of a hydrophilic material having the characteristics and accompanying advantages previously described above. In an optional embodiment, the electrode surgical probe may further comprising a fluid delivery conduit extending through the probe shaft in fluid communication with the coagulation electrode. In this manner, electrically conductive fluid may be readily provided to the coagulation electrode on demand without displacing the electrosurgical probe from the tissue site. Alternatively, the coagulation electrode may be repeatedly dipped in a source of electrically conductive fluid.

The electrosurgical probe further comprises a tissue resection member, such as a blunt resection member and/or resection electrode, mounted to the distal end of the probe shaft. The resection member has a leading surface configured for being placed along the leading surface of the coagulation electrode. The leading surface may be configured for protruding from the leading surface of the coagulation electrode to, e.g., enhance tissue resection. In an optional embodiment, the leading surface of the coagulation electrode is configured for being placed in contact with a tissue surface when the resection member is firmly placed in contact with the tissue surface. In this manner, tissue may be simultaneously coagulated and resected. In another optional embodiment, the leading surface of the resection member is configured for being embedded within the coagulation electrode when the leading surface of the coagulation electrode is lightly placed in contact with the tissue, and for protruding from the leading surface of the coagulation electrode when the leading surface of the coagulation electrode is firmly placed in contact with the tissue. In this manner, tissue can be selectively coagulated and/or resected, depending on the pressure applied at the electrode-tissue interface.

If the resection member is a resection electrode, it may be in electrical contact with the coagulation electrode in a monopolar configuration. Alternatively, the electrosurgical probe may comprise an electrical insulating member interposed between the resection electrode and the coagulation electrode, in which case, the resection electrode and coagulation electrode can be in a bipolar configuration. In addition to the typical advantages associated with configuring electrodes in a bipolar configuration, the resection electrode cannot be activated until the coagulation electrode absorbs a sufficient amount of electrically conductive fluid. In one embodiment, the electrical insulating member has a recess, in which case, the resection electrode may be seated within the recess.

In certain embodiments, the tissue resection member may be advantageously interposed between two coagulation electrode surfaces or two coagulation electrodes. For example, the coagulation electrode may include first and second leading surface portions, in which case, the leading surface of the resection member may be configured for being interposed therebetween. As another example, the electrosurgical probe may comprise another tissue coagulation electrode mounted to the distal end of the probe shaft. Like the first coagulation electrode, the other coagulation electrode is configured for absorbing an electrically conductive fluid, and has a leading surface that can be placed in contact with tissue. In this case, the leading surface of the resection member is configured for being interposed between the leading surface of the coagulation electrode and the leading surface of the other coagulation electrode.

In other embodiments, the electrosurgical probes may have additional tissue coagulation/resection surfaces. For example, the coagulation electrode may have another leading surface that can be placed in contact with tissue, in which case, the electrosurgical probe may further comprise another resection member mounted to the distal end of the probe shaft. The other resection member has a leading surface configured for being placed along the other leading surface of the coagulation electrode. As another example, the coagulation electrode has a leading distal surface, and the resection member and the other resection member form a loop that extends around the such leading distal surface.

In accordance with a third aspect of the present inventions, another electrosurgical probe is provided. The electrosurgical probe comprises an elongated probe shaft, which may be rigid, and a tissue resection member, such as a blunt resection member and/or resection electrode, mounted to the distal end of the probe shaft, and configured for being placed in contact with a tissue surface at a resection line. The electrosurgical probe further comprises at least one tissue coagulation electrode mounted to the distal end of the probe shaft, wherein the coagulation electrode(s) is configured for absorbing an electrically conductive fluid and for being placed in contact with the tissue surface on laterally opposite sides of the resection line. For example, a single coagulation electrode may have a pair of edge surface portions, in which case, the resection member will be interposed between the surface portions. Or the resection member may be interposed between a pair of coagulation electrodes. In either case, the coagulation electrode(s) may be composed of a hydrophilic material having the characteristics and accompanying advantages previously described above. As previously discussed above, the electrosurgical probe may comprise a fluid delivery conduit extending through the probe shaft in fluid communication with the coagulation electrode(s), or the coagulation electrode(s) may be dipped in a source of electrically conductive fluid. The detailed structure and relationship between the resection member and coagulation electrode(s) may be the same as that described above.

In accordance with a fourth aspect of the present inventions, a method of resecting tissue (e.g., highly vascularized tissue) using either of the previous two electrosurgical probes is provided. The method comprises absorbing the electrically conductive fluid into the coagulation electrode(s), conveying electrical energy to or from the coagulation electrode(s) to coagulate the tissue along a resection line, and manipulating the resection member to separate the tissue along the resection line. If the resection member is a resection electrode, electrical energy may be conveyed to or from the resection electrode to separate the tissue along the resection line. The electrical energy may be simultaneously conveyed to or from the coagulation electrode(s) and resection electrode, and/or may be conveyed between the coagulation electrode(s) and the resection electrode to coagulate and separate the tissue along the resection line.

In accordance with a fifth aspect of the present inventions, still another electrosurgical probe is provided. The electrosurgical probe comprises an elongated probe shaft, which may be rigid, and a pair of rigid opposing members distally extending from the probe shaft. The rigid members have respective inward facing surfaces that form a channel therebetween. At least one, but preferably both, of the inward facing surfaces have a taper, whereby a region of an anatomical vessel that proximally slides within the channel is gradually closed by the respective inward facing surfaces. In one embodiment, the rigid members may be fixed relative to each other, since the tapered inward facing surface of one or both of the rigid members effects the vessel compression.

The electrosurgical probe further comprises a first vessel ligation electrode adjacent the inward facing surface of one of the rigid members, wherein the first ligation electrode is configured for contacting a first side (e.g., a top side) of the anatomical vessel at the closed region. The electrosurgical probe further comprises a first hydrophilic electrode laterally disposed relative to the one opposing member, wherein the hydrophilic electrode is configured for contacting the first side (e.g., the top side) of the anatomical vessel when disposed within the channel. Whereas the first ligation electrode contacts the closed region of the anatomical vessel, the first hydrophilic electrode may contact the open region of the anatomical vessel due to its lateral disposition relative to the one rigid member. Although the present inventions should not be so limited in their broadest aspects, contact between the first ligation electrode and the closed region of the anatomical vessel allows larger anatomical vessels to be sealed, since electrical energy need only traverse the reduced thickness of the closed region.

In an optional embodiment, the electrosurgical probe comprises a second vessel ligation electrode adjacent the inward facing surface of another of the rigid members, wherein the second ligation electrode is configured for contacting a second side (e.g., a bottom side) opposite the first side of the anatomical vessel. In this case, the hydrophilic electrode may be laterally disposed relative to the other rigid member and be configured for contacting the second side (e.g., the bottom side) of the anatomical vessel when disposed within the channel.

In another optional embodiment, the electrosurgical probe further comprises a second hydrophilic electrode laterally disposed relative to the one rigid member, wherein the one rigid member is interposed between the first and second hydrophilic electrodes, and wherein the hydrophilic electrode is configured for contacting the first side of the anatomical vessel when disposed within the channel. In one embodiment, the ligation electrode(s) and hydrophilic electrode(s) are in a bipolar (multipolar) relationship with the previously discussed advantages. In this case, rigid members may be composed of an electrically insulative material, and may include recess(es) in which the ligation electrode(s) are respectively seated. The electrosurgical probe may comprise a fluid delivery conduit extending through the probe shaft in fluid communication with the coagulation electrode(s), or the coagulation electrode(s) may be dipped in a source of electrically conductive fluid.

In another optional embodiment, the rigid members have respective outward facing surfaces, in which case, the electrosurgical probe may further comprise a first tissue resection member (e.g., a blunt resection member and/or a resection electrode) adjacent the outward facing surface of one of the rigid members. A second tissue resection member can be provided adjacent the outward facing surface of another of the rigid members. If the resection member(s) are resection electrodes, the resection electrode(s) and the hydrophilic electrode(s) may be a bipolar (or multipolar) relationship with the previously discussed advantages. The first ligation electrode and first resection electrode may be conveniently formed by the same member, as well as the optional second ligation electrode and second resection electrode.

In accordance with a sixth aspect of the present inventions, yet another electrosurgical probe is provided. The electrosurgical probe comprises an elongated probe shaft and a pair of rigid, electrically insulative, opposing members distally extending from the probe shaft. The rigid members having inward facing surfaces that act to close an anatomical vessel in the same manner described above. The electrosurgical probe further comprises a metallic material disposed on the inward facing surfaces of the rigid members, a hydrophilic material disposed on the opposing lateral surfaces of each rigid member, and at least one connector terminal electrically coupled to the metallic material and hydrophilic material. The hydrophilic material may have the same characteristics as the previously described hydrophilic material with the associated advantages. As previously discussed above, the electrosurgical probe may comprise a fluid delivery conduit extending through the probe shaft in fluid communication with the hydrophilic material, or the hydrophilic material may be dipped in a source of electrically conductive fluid. The detailed structure and relationship between the metallic material and the hydrophilic material may be the same as that described above with respect to the ligation electrode(s) and coagulation electrode(s). The electrosurgical probe may also have tissue resection member(s) as previously described above.

In accordance with a seventh aspect of the present inventions, a method of ligating an anatomical vessel, e.g., a blood vessel, using either of the previous two electrosurgical probes is provided. The method comprises absorbing an electrically conductive fluid into the hydrophilic electrode (or hydrophilic material), sliding the anatomical vessel within the channel to close a region of the anatomical vessel between the inward facing surfaces of the rigid members, and conveying electrical energy between the ligation electrode (or electrically conductive material) and the hydrophilic electrode to seal the closed region of the anatomical vessel. An optional method comprises conveying electrical energy between the ligation electrode and the hydrophilic electrode to transect the closed region of the anatomical vessel. If the electrosurgical probe is provided with a resection member, the method may further comprise conveying electrical energy to or from the hydrophilic electrode to coagulate tissue along a resection line, and manipulating the resection member to separate the tissue along the resection line and expose the anatomical vessel on the resection line. The anatomical vessel can then be closed and sealed.

In accordance with an eighth aspect of the present inventions, yet another electrosurgical probe is provided. The electrosurgical probe comprises an elongated probe shaft, which may be rigid, and a rigid, electrically insulative, tissue dissection member distally extending from the probe shaft. As examples, the dissection may have a clamp-like profile or a hook-like profile. The dissection member has a pair of member portions having opposing inward facing surfaces that form a channel therebetween, whereby an anatomical vessel can be captured between the respective inward facing surfaces. Each rigid member also has opposing lateral surfaces.

The electrosurgical probe further comprises a hydrophilic material disposed on the opposing lateral surfaces of each of the rigid member portions, and at least one connector terminal electrically coupled to the hydrophilic material. In one embodiment, the hydrophilic material disposed on the opposite lateral surfaces are in a bipolar relationship. The hydrophilic material may have the same characteristics as the previously described hydrophilic material with the associated advantages. The electrosurgical probe may comprise a fluid delivery conduit extending through the probe shaft in fluid communication with the hydrophilic material, or the hydrophilic material may be dipped in a source of electrically conductive fluid. In an optional embodiment, the electrosurgical probe may comprise one or more electrodes adjacent one or more of the inward facing surfaces. In this case, the electrode(s) and hydrophilic material may be in a bipolar relationship with the previously discussed advantages.

In accordance with a ninth aspect of the present inventions, a method of ligating an anatomical vessel using the previously described electrosurgical probe is provided. The electrosurgical probe comprises absorbing the electrically conductive fluid into the hydrophilic material, capturing the anatomical vessel between the inward facing surfaces of the rigid member(s), and conveying electrical energy to or from the hydrophilic material to seal the anatomical vessel.

In accordance with a tenth aspect of the present inventions, yet another electrosurgical probe is provided. The electrosurgical probe comprises an elongated probe shaft, which may be rigid, and a rigid electrically insulative, member distally extending from the probe shaft. The electrosurgical probe further comprises a tissue coagulation electrode extending along one of the opposing surfaces of the rigid member, and a tissue cutting electrode (e.g., a wire) extending along another of the opposing surfaces of the rigid member. Although the present inventions should not be so limited, this configuration allows tissue coagulation and tissue cutting to be selectively effected with one electrosurgical probe. The coagulation electrode may optionally be composed of a hydrophilic material having the characteristics and accompanying advantages previously described above. As previously discussed above, the electrosurgical probe may comprise a fluid delivery conduit extending through the probe shaft in fluid communication with the coagulation electrode(s), or the coagulation electrode(s) may be dipped in a source of electrically conductive fluid. In one embodiment, the rigid member is straight, so that the cutting electrode and coagulation electrode are likewise straight and can therefore be placed along a straight resection line. The coagulation electrode and the cutting electrode may either be in a monopolar relationship or in a bipolar relationship. In the latter case, the coagulation electrode is configured to contact a tissue surface when the cutting electrode is firmly placed in contact with the tissue surface.

In accordance with an eleventh aspect of the present inventions, a method of resecting tissue, e.g., high vascularized tissue, using the previously described electrosurgical probe is provided. The method comprises conveying electrical energy to or from the coagulation electrode to coagulate the tissue along a resection line, and conveying electrical energy to or from the cutting electrode to cut the tissue along the resection line. In one method, the cutting electrode cuts the tissue while the coagulation electrode coagulates the cut tissue. In another method, the coagulation electrode coagulates the tissue, and then the cutting electrode cuts the coagulated tissue. In the case of a bipolar arrangement, the electrical energy can be conveyed between the cutting electrode and the coagulation electrode to cut the tissue.

In accordance with a twelfth aspect of the present inventions, yet another electrosurgical probe is provided. The electrosurgical probe comprises an elongated probe shaft, which may be rigid, a tapered tissue resection tip disposed at the distal end of the probe shaft, and a tissue coagulation electrode mounted to the distal end of the probe shaft axially proximal to the tissue resection tip. The coagulation electrode is configured for absorbing an electrically conductive fluid. The coagulation electrode may optionally be composed of a hydrophilic material having the characteristics and accompanying advantages previously described above. As previously discussed above, the electrosurgical probe may comprise a fluid delivery conduit extending through the probe shaft in fluid communication with the coagulation electrode(s), or the coagulation electrode(s) may be dipped in a source of electrically conductive fluid. The resection tip may be, e.g., a blunt resection tip or a resection electrode tip. In the later case, the electrode tip may be in electrical contact with the coagulation electrode in a monopolar configuration. Alternatively, an electrical insulating member may be interposed between the electrode tip and the coagulation electrode, in which case the electrode tip and coagulation electrode may be in a bipolar configuration. Although the present inventions should not be so limited in their broadest aspects, the axial relationship between the resection tip and the coagulation electrode allows tissue coagulation and resection to be accomplished during a single movement of the electrosurgical probe along a resection line.

In accordance with a thirteenth aspect of the present inventions, a method of resecting tissue, e.g., highly vascularized tissue, using the previously described electrosurgical probe is provided. The method comprises absorbing an electrically conductive fluid into the coagulation electrode, conveying electrical energy to or from the coagulation electrode to coagulate the tissue along the resection line, and manipulating the resection tip to separate the tissue along the resection line. In the case where the resection tip is an electrode tip, electrical energy can be conveyed to or from the electrode tip to separate the tissue along the resection line. In an optional method, the electrical energy can be simultaneously conveyed to or from the coagulation electrode and the resection electrode tip, and in the case of a bipolar arrangement, can be conveyed between the coagulation electrode and the resection electrode tip to coagulate and separate the tissue along the resection line.

Other and further aspects and features of the invention will be evident from reading the following detailed description of the preferred embodiments, which are intended to illustrate, not limit, the present inventions.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 2B is a perspective view of the tissue of FIG. 2A, wherein tissue along the resection line has been separated using the tissue coagulation/resection system of FIG. 1;

FIG. 2C is a perspective view of the tissue of FIG. 2A, wherein anatomical vessels have been exposed along the resection line by the tissue coagulation/resection system of FIG. 1;

FIG. 2D is a perspective of the tissue of FIG. 2A, wherein the unhealthy tissue portion has been completely resected from the healthy portion using the tissue coagulation/resection system of FIG. 1;

FIG. 6 is a cross-sectional view of another embodiment of a tissue coagulation/resection assembly that can disposed on the probe used in the tissue coagulation/resection system of FIG. 1, particularly showing a tissue resection electrode recessed within a tissue coagulation electrode;

FIG. 7 is a cross-sectional view of the tissue coagulation/resection assembly of FIG. 6, particularly showing the tissue resection electrode protruding from the tissue coagulation electrode;

FIG. 8 is a cross-sectional view of the tissue coagulation/resection assembly of FIG. 6, particularly showing the monopolar conveyance of electrical energy to coagulate and separate the tissue;

FIG. 9 is a cross-sectional view of the tissue coagulation/resection assembly of FIG. 6, particularly showing the monopolar conveyance of electrical energy to only coagulate the tissue;

FIG. 17 is a side view of yet another embodiment of a tissue coagulation/resection assembly that can disposed on the probe used in the tissue coagulation/resection system of FIG. 1;

FIG. 18 is a cross-sectional view of the tissue coagulation/resection assembly of FIG. 13;

FIG. 19 is a cross-sectional view of the tissue coagulation/resection assembly of FIG. 17, particularly showing the monopolar conveyance of electrical energy to coagulate and separate the tissue;

FIG. 20 is a cross-sectional view of the tissue coagulation/resection assembly of FIG. 17, particularly showing the bipolar conveyance of electrical energy to coagulate and separate the tissue;

DETAILED DESCRIPTION OF THE ILLUSTRATED EMBODIMENTS

Figure 1:
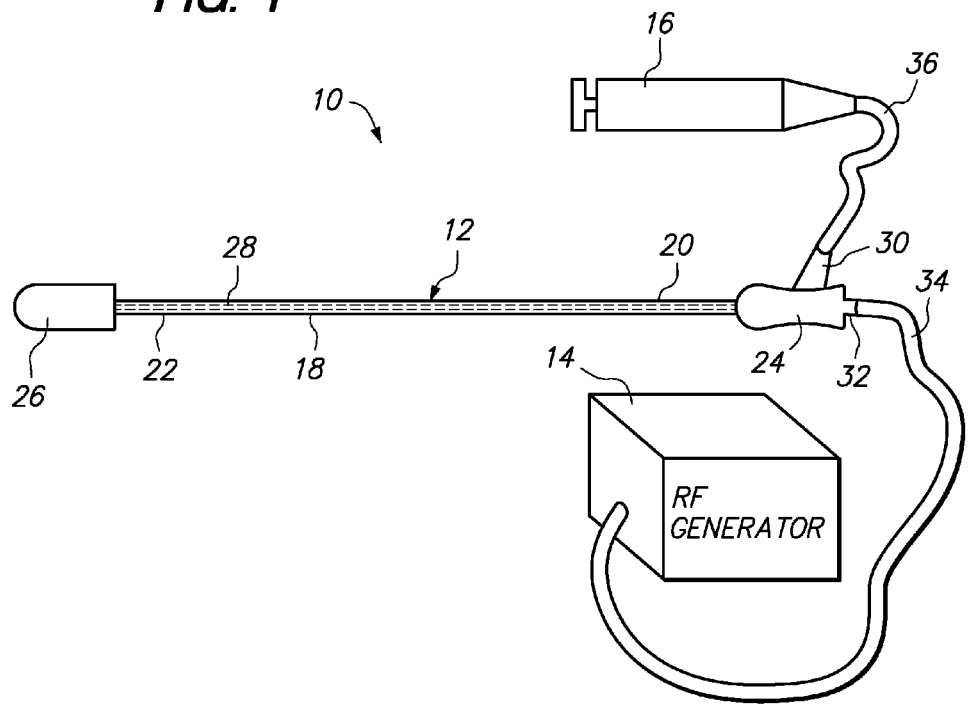
FIG. 1 is a plan view of a tissue coagulation/resection system constructed in accordance with one preferred embodiment of the present invention.

FIG. 1 illustrates a tissue resection system 10 constructed in accordance with a preferred embodiment of the present inventions. The tissue resection system 10 generally comprises tissue coagulation/resection probe 12 configured for coagulating and resecting tissue, an ablation energy source, and in particular a radio frequency (RF) generator 14, configured for supplying RF energy to the tissue resection probe 12 in a controlled manner, and an electrically conductive fluid source, and in particular a syringe 16 configured for supplying electrically conductive fluid (e.g., saline) to the resection probe 12 to provide an electrically conductive path for the RF energy from the resection probe 12 to the tissue to be coagulated/resected.

The coagulation/resection probe 12 generally comprises an elongated probe shaft 18 having a proximal end 20, a distal end 22, a handle assembly 24 mounted to the proximal shaft end 20, a tissue coagulation/resection assembly 26 mounted to the distal shaft end 22, and a fluid conduit 28 (shown in phantom) extending through the probe shaft 18 between the proximal shaft end 20 and the probe distal end 22. In the illustrated embodiment, the probe shaft 18 is rigid, thereby providing maximum control at the distal end 22 of the probe shaft 18. The probe shaft 18 is composed of a suitable material, such as plastic, metal or the like, and has a suitable length, typically in the range from 5 cm to 30 cm, preferably from 10 cm to 20 cm. If composed of an electrically conductive material, the probe shaft 18 is preferably covered with an insulative material (not shown). The probe shaft 18 has an outside diameter consistent with its intended use.

The tissue coagulation/resection assembly 26 comprises a tissue coagulation electrode and a tissue resection member, both of which can have a variety of structures and forms, as shown in the specific embodiments described below The coagulation electrode may be used to coagulate tissue along a resection line, and the tissue resection member may be used to separate the tissue along the resection line. In certain embodiments, the tissue coagulation/resection assembly 26 may be used to seal and/or transect anatomical vessels, such as blood vessels, that have been exposed along the resection line.

The coagulation electrode has one or more leading surfaces that are configured for contacting tissue, and is hydrophilic in that it is configured for absorbing an electrically conductive fluid, such as saline. In the illustrated embodiment, the leading surfaces are straight or rectilinear, so that they can be placed along a resection line. It is preferred that the material used in the coagulation electrode be capable of absorbing an amount of liquid at least equal to its dry weight, preferably an amount at least equal to at least two times its dry weight, and more preferably an amount at least equal to at least four times its dry weight. In general, the more liquid absorbed per unit weight of the coagulation electrode, the more electrically conductive the electrode.

Suitable materials that can be used to construct the coagulation electrode include open-cell foam (such as polyethylene foam, polyurethane foam, polyvinylchloride foam) and medical-grade sponges. In the illustrated embodiment, a foam composed of Hypol 3000 base polymer marketed by W.R. Grace & Co, an L-62 Surfactant marketed by BASF Corporation, and water is used. It has been found that the open-cell polyurethane foam marketed by Avitar, Inc. as Hydrosorb™ is especially suitable, and is capable of absorbing an amount of liquid twenty times its dry weight. Polyvinyl acetal sponges, such as Merocel™, marketed by Medtronic, Inc., and cellulose sponges, such as Weckcel™ are also suitable. It should be appreciated that material, other than foam or sponges, may be used for the coagulation electrode as long as it is capable of absorbing a sufficient amount of liquid. For example, spun-laced polyester, cotton, gauze, cellulose fiber, or the like can be used.

It can be appreciated that, although suitable materials used in the coagulation electrode will typically be electrically insulative, the electrode will become electrically conductive upon absorption of electrically conductive fluid. This is advantageous because the coagulation electrode cannot be activated until it absorbs a sufficient amount of electrically conductive fluid. Thus, unlike other electrosurgical systems that utilize saline, the inactivation of the electrode will prevent tissue charring from occurring if the flow of saline is cutoff or is otherwise insufficient. In addition, because the absorbent nature of the coagulation electrode provides only the necessary amount of electrically conductive fluid to the tissue site by limiting the electrically conductive fluid to the tissue-electrode interface, the electrical energy conveyed by the electrode is focused at the desired location, and aspiration of electrically conductive fluid, which may otherwise accumulate at the tissue using other saline systems, is obviated.

The tissue resection member has a leading surface, which in some embodiments, may be interposed between a pair of leading surfaces of the coagulation electrode, as will be described in further detail below. In the illustrated embodiment, the leading surface is straight or rectilinear, so that it can be placed along a resection line. The tissue resection member may be a blunt resection member, which means that tissue separation may be achieved by mechanically manipulating the tissue with the resection member, or a resection electrode, which means that tissue separation may be achieved by conveying electrical energy to or from the resection member to either cut the tissue or coagulate the tissue. If the resection member operates to coagulate the tissue, the mechanical pressure applied by the resection member may naturally separate the tissue as it is coagulated. As will be described in further detail below, electrical energy can either be conveyed from the resection electrode in a monopolar mode, or conveyed between the resection electrode and the coagulation electrode in a bipolar mode.

In the monopolar mode, RF current is delivered from the RF generator 14 to the coagulation electrode, and if applicable the resection electrode, which means that current will pass from the respective electrode, which is configured to concentrate the energy flux in order to have an injurious effect on the surrounding tissue, and a dispersive electrode (not shown), which is located remotely from the electrode and has a sufficiently large area (typically 130 cm² for an adult), so that the current density is low and non-injurious to surrounding tissue. In the illustrated embodiment, the dispersive electrode may be attached externally to the patient, e.g., using a contact.

In a bipolar mode, the RF current is delivered between the coagulation electrode and another electrode, such as a resection electrode, with one of the electrodes being the "positive" electrode element and the other of the electrodes being the "negative" electrode element. Bipolar arrangements, which require the RF energy to traverse through a relatively small amount of tissue between the tightly spaced electrodes, are more efficient than monopolar arrangements, which require the RF energy to traverse through the thickness of the patient's body. As a result, bipolar electrode arrangements are generally more efficient than monopolar electrode arrangements. Additionally, bipolar arrangements are generally safer for the physician and patient, since there is an ever-present danger that the physician and patient may become a ground in the monopolar arrangement, resulting in painful burns.

The handle assembly 24 is composed of any suitable rigid material, such as, e.g., metal, plastic, or the like. The handle assembly 24 carries a perfusion port 30, which is in fluid communication with the fluid delivery conduit 28, which is further in fluid communication with the coagulation electrode. The handle assembly 24 further carries an electrical connector 32 that is electrically coupled to the coagulation electrode via the probe shaft 18. In this case, the core of the probe shaft 18 is composed of an electrically conductive material, such as stainless steel, and the exterior of the probe shaft 18 is coated with an electrically insulative material (not shown). Alternatively, the electrical connector 32 may be electrically coupled to the coagulation electrode via wires (not shown) extending through the probe shaft 18 and terminating within the coagulation electrode or in the shaft distal end 22 (which will be electrically conductive in this case) on which the coagulation electrode is directly mounted.

If the resection member is an resection electrode, the electrical connector 32 may also be electrically coupled to the resection electrode, the manner of which will depend on whether the resection electrode is in a monopolar or bipolar configuration.

If a monopolar configuration is used, the electrical connector 32 may be electrically coupled to the resection electrode via the probe shaft 18. If the coagulation electrode and resection electrode are simultaneously activated, the probe shaft 18 may be used to conduct the electrical energy to both the coagulation electrode and resection electrode. If the coagulation electrode and resection electrode are designed to be serially activated, or otherwise must remain electrically isolated, the electrical connector 32 may be coupled to one of the coagulation electrode and resection electrode via wires (not shown) and to the other of the coagulation electrode and resection electrode via the probe shaft 18. Alternatively, the electrical connector 32 may be coupled to the respective coagulation electrode and resection electrode via separate wires.

If a bipolar configuration is used, the electrical connector 32 may be electrically coupled to the coagulation electrode and resection electrode via the probe shaft 18 or wires as long as the respective electrodes are electrically isolated from each other. In this case, the electrical connector 32 is configured, such that one of the electrodes can be coupled to a positive pole of the RF generator 14, and the other of the electrodes can be coupled to a negative pole of the RF generator 14.

The RF generator 14 is electrically connected to the electrical connector 32 on the probe 12 via a cable 34. The RF generator 14 may be a conventional RF power supply that operates at a frequency in the range from 200 KHz to 9.5

MHz, with a conventional sinusoidal or non-sinusoidal wave form. Such power supplies are available from many commercial suppliers, such as Valleylab, Aspen, Bovie, and Ellman. Most general purpose electrosurgical power supplies, however, operate at higher voltages and powers than would normally be necessary or suitable for tissue coagulation and/or cutting. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000 (100 W) and RF3000 (200 W). Optionally, the RF generator 14 may include means for conveying the RF energy in a "coagulation mode" or a "cutting mode." As previously described, operating an RF generator in a coagulation mode will tend to create a tissue coagulation effect, while operating an RF generator in a cutting mode will tend to create a tissue cutting effect, although tissue coagulation or cutting will ultimately depend, to a greater extent, on the structure of the electrode to or from which the electrical energy is conveyed.

The syringe 16 is connected to the perfusion port 30 on the probe 12 via tubing 36. As briefly discussed above, the syringe 16 contains an electrically conductive fluid, such as saline. The syringe 16 is conventional and is of a suitable size, e.g., 200 ml. In the illustrated embodiment, the electrically conductive fluid is 0.9% saline. Thus, it can be appreciated the syringe 16 can be operated to convey the saline through the tubing 36, into the perfusion port 30, through the fluid delivery conduit 28 extending through the inner probe shaft 18, and into contact with the coagulation electrode. The normally electrically insulative material of the coagulation electrode, in turn, absorbs the saline, thereby creating an electrical path through the insulative material and transforming the electrode into an electrically conductive element.

Having described the general structure and function of the tissue resection system 10, its operation in resecting tissue will be described. The tissue may be located anywhere in the body where resection may be beneficial. Most commonly, the tissue will contain a solid tumor within an organ of the body, such as the liver, kidney, pancreas, breast, prostrate (not accessed via the urethra), and the like. In this case, an unhealthy tissue portion, e.g., a cancerous portion containing a tumor, e.g., a lobe of a liver, may be resected from the healthy portion of the tissue. In the preferred method, access to the tissue may be accomplished through a surgical opening to facilitate movement of the resection probe within the patient as well as to facilitate removal of the resected tissue from the patient. However, access to the tissue may alternatively be provided through a percutaneous opening, e.g., laparoscopically, in which case, the tissue resection probe can be introduced into the patient through a cannula, and the removed tissue may be minsilated and aspirated from the patient through the cannula.

The operation of the tissue resection system 10 is described in resecting unhealthy portion of tissue to be removed from a patient, which has a tumor, from a healthy portion of tissue to be retained within the patient. First, the RF generator 14 and associated cable 34 are connected to the electrical connector 24 on the probe 12, and the syringe 16 and associated tubing 36 are connected to the perfusion port 30 on the probe 12. The syringe 16 is then operated, such that the saline is conveyed under positive pressure, through the tubing 36, and into the perfusion port 30. The saline travels through the fluid conduit 28 within the probe shaft 18, and into contact with the coagulation electrode, where it is absorbed. As a result, the coagulation electrode becomes electrically conductive. Although perfusing the coagulation electrode with electrically conductive fluid under pressure from the syringe 16 or any suitable pumping mechanism provides a convenient means for making the coagulation electrode electrically conductive and maintaining it as such, the coagulation electrode may simply be repeatedly dipped into a supply of electrically conductive fluid if such perfusion means is not available.

Figure 2A:
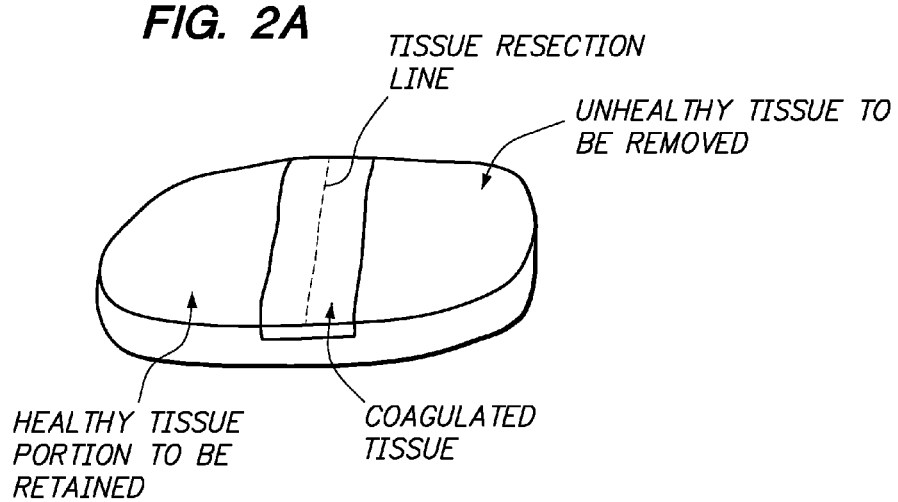
FIG. 2A is a perspective view of tissue having an unhealthy tissue portion to be resected from a healthy tissue portion, wherein tissue along a resection line has been coagulated using the tissue coagulation/resection system of FIG. 1.

Next, the resection probe 12 is manipulated, such that the coagulation electrode is moved in proximity to the tissue along opposite lateral sides of a resection line, and RF energy is conveyed between the RF generator 14 and the coagulation electrode, resulting in the coagulation of the tissue adjacent a resection line, as illustrated in FIG. 2A. In particular, electrical energy is conveyed to or from the coagulation electrode through the tissue along the resection line, thereby coagulating a band of tissue that straddles the resection line. The coagulation electrode may be placed in direct contact with the tissue, or alternatively, if the voltage is great enough, may be moved just above the tissue, such that arcing occurs between the coagulation electrode and tissue. In a monopolar arrangement, RF energy will be conveyed from the RF generator 14 to the coagulation electrode, whereas in a bipolar arrangement, the RF energy may be conveyed from the RF generator 14 to the coagulation electrode or from the coagulation electrode to the RF generator 14, depending on whether the coagulation electrode is coupled to the positive pole or negative pole of the RF generator 14.

Next, the coagulated tissue along the resection line is separated, as illustrated in FIG. 2B. In the illustrated method, the coagulated tissue is separated using the tissue resection member. Tissue separation can either be mechanically achieved (in the case where the resection member is a blunt resection member) and/or electrically achieved (in the case where the resection member is a resection electrode). In either case, separation of the coagulated tissue can be achieved by running the resection member along the resection line. In the case of mechanical resection, physical pressure will need to be applied to the tissue by the resection member. In the case of electrical resection, no physical pressure (e.g., if the resection electrode is designed to cut) or very little physical pressure is required to be applied to the tissue by the resection member. Instead, the RF energy conveyed between the tissue and resection electrode provides most, if not all, of the tissue resection energy.

Separation of the tissue can be accomplished in a separate step after tissue coagulation has been achieved, or can be achieved as tissue coagulation is taking place. In the latter case, the resection member is moved with the coagulation electrode along the resection line to separate the tissue that is being coagulated by the coagulation electrode. If the resection member is a resection electrode, RF energy can be simultaneously conveyed to or from the coagulation electrode and resection electrode either in a monopolar mode or a bipolar mode.

Although not as expeditious or efficient as if a resection member is provided on the same probe as the coagulation electrode, in cases where a resection member is not provided on the resection probe 12, the tissue may be separated using a separate resection member, whether mechanical or electrical, or may be even be separated using the coagulation electrode itself. In the latter case, the tissue may be held under tension, such that resection naturally occurs along the resection line as the adjacent tissue is weakened by coagulation.

During tissue coagulation and separation, there may be anatomical vessels, such as blood vessels, that traverse the resection line, as illustrated in FIG. 2C. Notably, because blood vessels are mostly composed of collagen, they will typically remain intact even through the surrounding tissue (e.g., the parenthymia of an organ) does separate, resulting in the skeletalization of the tissue. In this case, the tissue resection probe 12 may be used to seal the portion of the blood vessel that traverses the resection line. The sealed portion of the blood vessel can then be transected, as illustrated in FIG. 2D, using either the tissue resection probe 12 or a separate device, such as scissors. The tissue coagulation and separation steps can be repeated until the unhealthy tissue portion has been completely resected from the healthy tissue portion.

Figure 3:
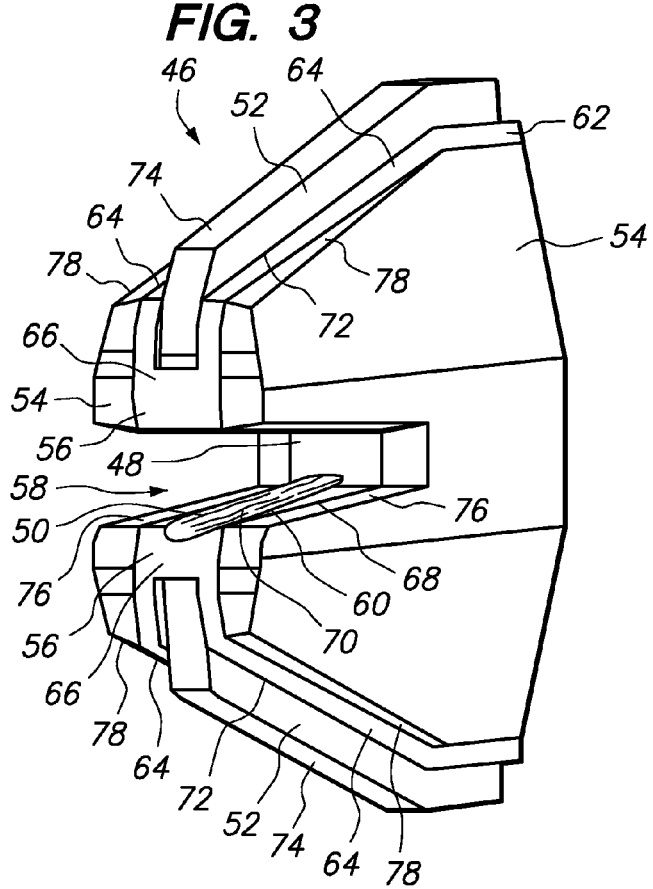
FIG. 3 is a perspective view of one embodiment of a tissue coagulation/resection assembly that can disposed on the probe used in the tissue coagulation/resection system of FIG. 1.

Having described the general structure and operation of the tissue ablation system 10, specific embodiments of the tissue coagulation/resection assembly will now be described. Referring to FIG. 3, an embodiment of a tissue coagulation/resection assembly 46 constructed in accordance with one embodiment of the present inventions is described. The coagulation/resection assembly 46 generally comprises a blunt tissue dissection member 48 suitably mounted to the distal end of the probe shaft 18 (shown in FIG. 1), and a pair of vessel ligation electrodes 50 (only one shown), a pair of tissue resection electrodes 52, and a pair of tissue coagulation electrodes 54 mounted to the dissection member 48.

The dissection member 48 can be composed of any suitable rigid material, but in the illustrated embodiment, is composed of an electrically insulative material, such as polyether ether ketone (PEEK), polytetrafluoroethylene (PTFE), polyoxymethylene (POM), polyamide, polyamide-imide (PAI), polybutadiene, polycarbonate (PC), or polypropylene (PP), to maintain electrical isolation between the coagulation electrodes 54 and the ligation and resection electrodes 50, 52, as will be described in further detail below. In the illustrated embodiment, the dissection member 48 is composed of a unibody structure, although in alternative embodiments, the dissection member 48 may comprise distinct pieces. Any suitable process, such as injection molding, can be used to form the dissection member 48.

Figure 4:
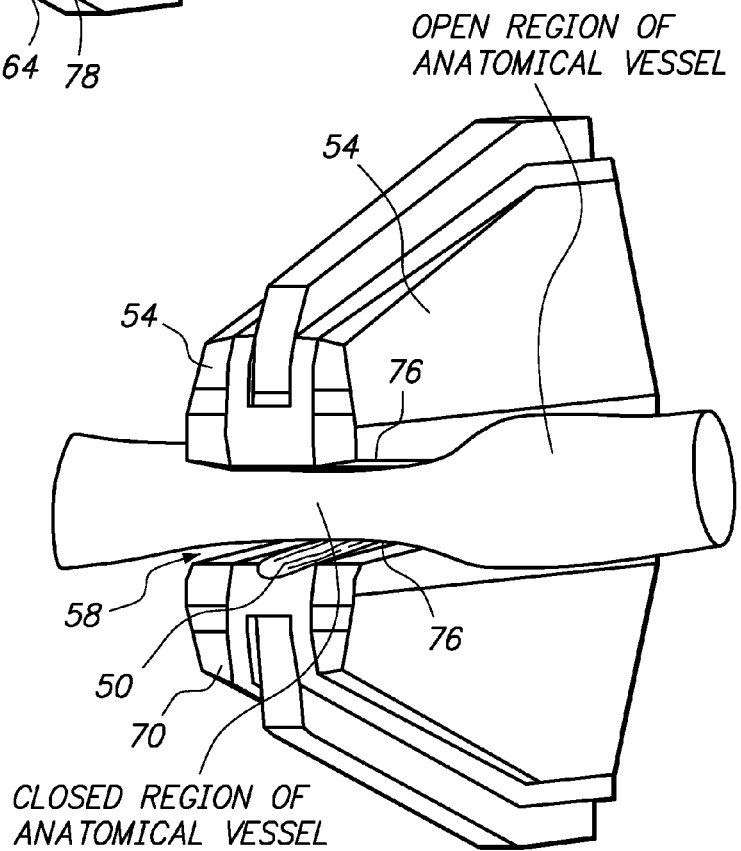
FIG. 4 is a perspective view of the tissue coagulation/resection assembly of FIG. 3, particularly showing an anatomical vessel compressed and captured.

The dissection member 48 has a clamp-like profile, and in particular, includes a pair of opposing rigid member portions 56 that form a channel 58 therebetween where anatomical vessels, such as blood vessels, can be compressed and closed. The dissection member 48 has a pair of opposing, flat, inward facing surfaces 60, a pair of opposing, flat, lateral surfaces 62 (only one shown), and a pair of opposing, flat, outward facing surfaces 64. In the illustrated embodiment, the rigid member portions 56 need not move relative to each other to effect this clamping function. Instead, the rigid member portions 56 are fixed relative to each other, and the inward facing surfaces 60 taper, so that the channel 58 gradually narrows in the proximal direction. In this manner, a region of an anatomical vessel that proximally slides within the channel 58 is gradually closed by the respective inward facing surfaces 60, as illustrated in FIG. 4. Alternatively, only the inward facing surface 60 of one of the rigid member portions 56 is tapered in this manner, so that the channel 58 gradually narrows in the proximal direction. The rigid member portions 56 also have rounded tips 66 that can be used as blunt tissue dissection members.

In the illustrated embodiment, the ligation electrodes 50 are composed of a biocompatible and electrically conductive and material, such as stainless steel, gold, platinum, or alloys thereof, and are located adjacent the inward facing surfaces 60 of the respective rigid member portions 56. In the illustrated embodiment, each rigid member portion 56 has a recess 68 (only one shown) formed within the respective inward facing surface 60. The ligation electrodes 50 are seated within the recesses 68 of the respective rigid member portions 56, so that a leading surface 70 of the ligation electrodes 50 are exposed and flush with the respective inward facing surfaces 60 of the dissection member 48. In this manner, the inward facing surfaces 70 of the ligation electrodes 50 are configured for contacting opposite sides (i.e., top and bottom) of the closed region of the anatomical vessel disposed within the channel 58, as illustrated in FIG. 4. Thus, it can be appreciated that, because electrical energy need only traverse the reduced closed region of an anatomical vessel, larger anatomical vessels may be sealed with the ligation electrodes 50. The width of each ligation electrode 50 may be narrow to facilitate optional transection of the anatomical vessel.

In the illustrated embodiment, each recess 60, and thus, each ligation electrode 50, substantially extends the length of the respective rigid member portion 56, so that the ligation electrodes 50 contact the anatomical vessel wherever located within the channel 58. While it is preferable to have a pair of opposing ligation electrodes 50, in alternative embodiments, only one ligation electrode 50 is provided. The ligation electrodes 50 may be coupled to the electrical connector 32 via the probe shaft 18 (shown in FIG. 1) or wires (not shown). Although electrical energy may be delivered to the ligation electrodes 50 in a monopolar configuration, in the illustrated embodiment, electrical energy is delivered between the ligation electrodes 50 and coagulation electrodes 54 in a bipolar configuration to facilitate vessel ligation.

In the illustrated embodiment, the resection electrodes 52 are composed of a biocompatible, electrically conductive, rigid material, such as stainless steel, gold, platinum, or alloys thereof, and are located adjacent the outward facing surfaces 64 of the dissection member 48. In the illustrated embodiment, each rigid member portion 56 has a recess 72 formed within the respective outward facing surface 64. Each resection electrode 52 is seated within the recess 72 of the respective rigid member portion 56, so that a leading surface 74 of the resection electrodes 52 protrudes from the respective outward facing surfaces 64 of the dissection member 48. In this manner, the resection electrodes 52 are configured for embedding within the surface of tissue, thereby enhancing the tissue resecting effect. In the illustrated embodiment, each recess 72, and thus, each resection electrode 52, substantially extends the length of the respective rigid member portion 56. While it is preferable to have a pair of resection electrodes 52, in alternative embodiments, only one resection electrode 52 is provided.

The resection electrodes 52 may be coupled to the electrical connector 32 via the probe shaft 18 (shown in FIG. 1) or wires (not shown). Although electrical energy may be delivered to the resection electrodes 52 in a monopolar configuration, in the illustrated embodiment, electrical energy is delivered between the resection electrodes 52 and coagulation electrodes 54 in a bipolar configuration to facilitate tissue resection. The resection electrodes 52 and ligation electrodes 50 may be electrically coupled together, so that electrical energy can be simultaneously delivered to or from the ligation and resection electrodes 50, 52. Alternatively, one or both of the resection electrodes 52 can be replaced with a blunt resection member that generally takes the same form and shape as the illustrated resection electrodes 52, but are not configured to transmit or receive electrical energy.

The coagulation electrodes 54 are composed of a hydrophilic material, which, as previously discussed, is configured for absorbing an electrically conductive fluid, and may be composed of any one of a variety of materials, such as foam. The coagulation electrodes 54 may be coupled to the syringe 16 via the perfusion port 30 extending through the probe shaft 18 (shown in FIG. 1). A plurality of ports (not shown) may be provided within the lateral surfaces 62 of the dissection member 48 to facilitate distribution of the electrically conductive fluid within the coagulation electrodes 54 via the dissection member 48. The coagulation electrodes 54 may be coupled to the electrical connector 32 via the probe shaft 18 (shown in FIG. 1) or wires (not shown). Although electrical energy may be delivered to the coagulation electrodes 54 in a monopolar configuration, in the illustrated embodiment, electrical energy is delivered between the ligation and/or resection electrodes 50, 52 and the coagulation electrodes 54 in a bipolar configuration to facilitate vessel ligation/tissue resection.

In particular, the coagulation electrodes 54 may be configured for being placed within a bipolar (or multi-polar) relationship with the ligation electrodes 50 or resection electrodes 52 to facilitate vessel ligation and tissue resection. To this end, the coagulation electrodes 54 and ligation electrodes 50 are configured for being simultaneously placed in contact with an anatomical vessel, and the coagulation electrodes 54 and resection electrodes 52 are configured for being simultaneously placed in contact with tissue to be resected.

In particular, the dissection member 48 is interposed between the coagulation electrodes 54, such that the coagulation electrodes 54 are laterally disposed relative to the dissection member 48. The coagulation electrodes 54 are suitably mounted, e.g., via bonding, to the lateral surfaces 62 of the dissection member 48. In this manner, the coagulation electrodes 54 are configured for contacting the open regions of an anatomical vessel laterally opposite the region of the anatomical vessel closed within the channel 58, with each coagulation electrode 54 having a pair of inward facing leading surfaces 76 configured for contacting opposite sides (i.e., top and bottom) of the anatomical vessel, as illustrated in FIG. 4. Each coagulation electrode 54 also has a pair of outward facing leading surfaces 78 configured for contacting a surface of tissue to be resected laterally opposite of each resection electrode 52.

In the illustrated embodiment, the profiles of the coagulation electrodes 54 are geometrically similar to the profile of the dissection member 48. The inward facing surfaces 60 of each coagulation electrode 54 outwardly offset from the respective inward facing surfaces 60 of the dissection member 48 a small amount. Thus, it can be appreciated that the coagulation electrodes 54 will not hinder disposition of the anatomical vessel within the channel 58 of the dissection member 48, while ensuring that contact between the coagulation electrodes 54 and anatomical vessel is achieved. Alternatively, the inward facing surfaces 60 of the coagulation electrodes 54 may be flush with, or even inwardly offset a small amount from, the inward facing surfaces 60 of the dissection member 48, as long as the coagulation electrodes 54 do not hinder disposition of the anatomical vessel within the channel 58, while still ensuring contact with the anatomical vessel when closed between the rigid member portions 56.

The outward facing surfaces 64 of each coagulation electrode 54 are inwardly offset from the respective outward facing surfaces 64 of the dissection member 48 by a small amount, and the respective resection electrodes 52 protrude from the outward facing surfaces 64 of the respective coagulation electrodes 54. Contact between tissue to be resected and the coagulation electrodes 54 is achieved when the interposed resection electrode 52 is firmly placed in contact with the tissue. That is, the outward facing surface 74 of the resection electrode 52 depresses the tissue to the extent that the outward facing surfaces 64 of the coagulation electrodes 54 contact the tissue at the periphery of the depression. Alternatively, the outward facing surfaces 64 of the coagulation electrodes 54 may be flush with, or even outwardly offset from, the outward facing surfaces 64 of the dissection member 48 as long as they can contact tissue to be resected simultaneously with the respective resection electrode 52. In this case, because the resection electrode 52 is rigid, it can apply firm pressure to the tissue, even though the coagulation electrode 54, which is preferably compliant, also contacts the tissue.

Although FIG. 3 illustrates one coagulation electrode 54 mounted to a lateral surface of the dissection member 48, it should be appreciated that multiple coagulation electrodes 54 can be mounted to each lateral surface of the dissection member 48. For example, an upper coagulation electrode can be mounted to a lateral surface of the upper rigid member portion 56, and a lower coagulation electrode can be mounted to a lateral surface of the lower rigid member portion 56.

Figure 5A:
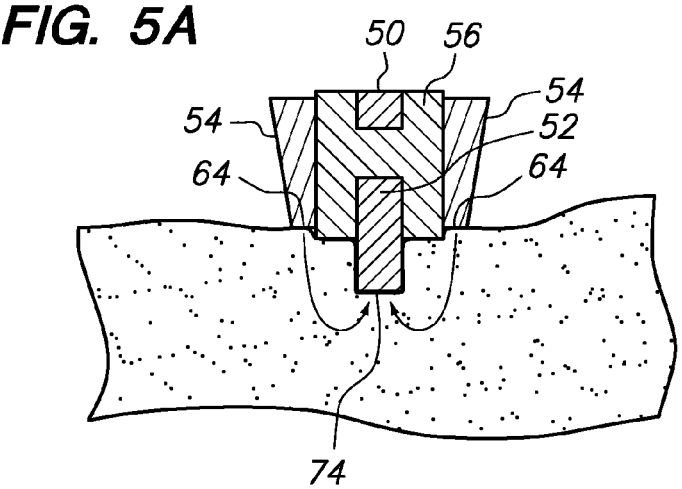
FIG. 5A is a cross-sectional view of the tissue coagulation/resection assembly of FIG. 3, particularly showing the bipolar conveyance of electrical energy through the tissue.
Figure 5B:
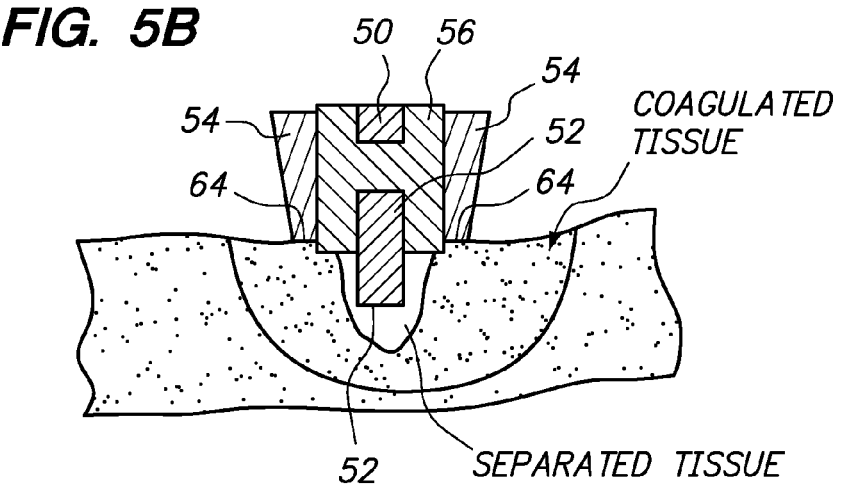
FIG. 5B is a cross-sectional view of the tissue coagulation/resection assembly of FIG. 3, particularly showing the tissue coagulated and separated.

One method of using tissue coagulation/resection assembly 46 will now be described in performing a tissue resection. The method comprises absorbing an electrically conductive fluid into the coagulation electrodes 54, e.g., by perfusing the coagulation electrodes 54 with the electrically conductive fluid via the perfusion port 30 (shown in FIG. 1) and/or dipping the coagulation electrodes 54 into the electrically conductive fluid. The outward facing surface 74 of one of the resection electrodes 52 is placed in contact with the tissue on the resection line, and the outward facing surfaces 64 of the coagulation electrodes 54 are placed in contact with the tissue on opposite lateral sides of the resection line. Electrical energy is then conveyed between the coagulation electrodes 54 and resection electrodes 52 as the tissue coagulation/resection assembly 46 is moved along the tissue resection line. In this manner, tissue adjacent the resection line is coagulated by the coagulation electrodes 54, while the tissue along the resection line is separated by the resection electrode 52. In particular, as illustrated in FIG. 5A, electrical energy (shown by arrows) is conveyed from the respective coagulation electrodes 54, through the tissue adjacent the resection line, and to the resection electrode 52. As a result, the electrical energy at the interface between the tissue surface and the outward facing surfaces 64 of the coagulation electrodes 54 coagulates a band of tissue along the resection line, and the electrical energy at the interface between the tissue surface and the resection electrode 52 separates the coagulated band of tissue along the resection line, as illustrated in FIG. 5B.

Alternatively, if the coagulation electrodes 54 in a monopolar configuration, electrical energy can be conveyed to or from one of the coagulation electrodes 54, while a different portion of that coagulation electrode 54, e.g., a lateral surface of the coagulation electrode 54, is placed on opposite lateral sides of the resection line to coagulate the adjacent tissue. One of the resection electrodes 52 can then be used to separate the coagulated tissue along the resection line. Electrical energy can be conveyed to or from the resection electrode 52 to electrically resect the tissue, or the resection electrode 52 can be used as a blunt resection member to separate the tissue along the resection line.

Figure 5C:
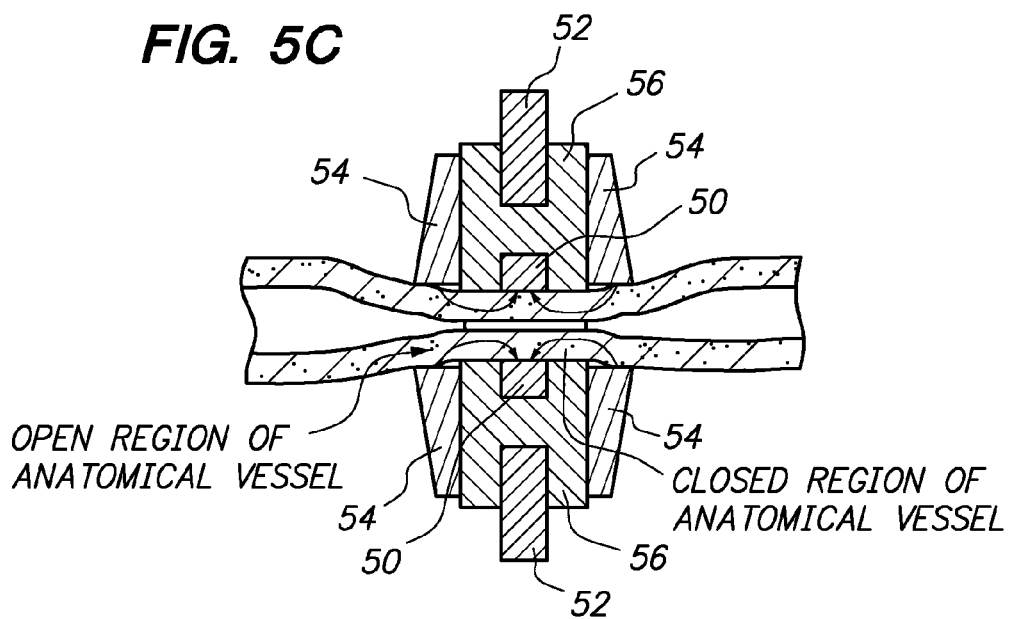
FIG. 5C is a cross-sectional view of the tissue coagulation/resection assembly of FIG. 3, particularly showing an anatomical vessel ligated.

When an anatomical vessel, such as a blood vessel, is encountered, the anatomical vessel can be slid within the channel 58 until the vessel is compressed and closed between the inward facing surfaces 60 of the dissection member 48. Electrical energy is then conveyed between the coagulation electrodes 54 and ligation electrodes 50 to seal the closed region of the anatomical vessel. In particular, as illustrated in FIG. 5C, electrical energy (shown by arrows) is conveyed from the respective coagulation electrodes 54, through the vessel tissue, and to the ligation electrodes 50. As a result, the electrical energy at the interface between the top side of the closed region of the vessel and the upper ligation electrode 50, and the electrical energy at the interface between the bottom side of the closed region of the vessel and the lower ligation electrode 50 causes the top and bottom sides of the closed vessel region to seal.

Depending on its diameter, the closed region of the anatomical vessel may be transected by the ligation electrodes 50. For example, it is expected that an anatomical vessel having a diameter of 3 mm or less may be completely transected by the ligation electrodes 50, whereas an anatomical vessel having a diameter greater than 3 mm will only be sealed by the ligation electrodes 50, and will then need to be transected with another device, such as scissors.

Referring to FIGS. 6 and 7, an embodiment of a tissue coagulation/resection assembly 86 constructed in accordance with another embodiment of the present inventions is described. The coagulation/resection assembly 86 generally comprises a coagulation electrode 88 and a tissue resection electrode 90.

The coagulation electrode 88 is composed of a hydrophilic material, which, as previously discussed, is configured for absorbing an electrically conductive fluid, and may be composed of any one of a variety of materials, such as foam. The coagulation electrode 88 may have any one of a variety of shapes, but in the embodiment illustrated in FIG. 7, has a trapezoidal cross-sectional shape with an upper leading surface 92, opposing lateral leading surfaces 94, and a lower leading surface 96, any of which can be placed in contact with tissue to effect a coagulation function. The coagulation electrode 88 may be coupled to the syringe 16 via the perfusion port 30 extending through the probe shaft 18 (shown in FIG. 1).

The tissue resection electrode 90 takes the form of a wire or rod composed of a biocompatible and electrically conductive and material, such as stainless steel, gold, platinum, or alloys thereof. The resection electrode 90 has a leading surface 98 that can be placed in contact with tissue to effect a tissue resection function. The tissue resection electrode 90 is laterally rigid, i.e., has a shear strength, so that it resists bending when placed in firm contact with tissue. The tissue resection electrode 90 is embedded within the coagulation electrode 88. In particular, the coagulation electrode 88 has a recess 100 that divides the lower surface 96 into a pair of lower surface portions. The tissue resection electrode 90 is suitably mounted, e.g., via bonding, within the recess 100. The hydrophilic material used to fabricate the coagulation electrode 88 is compressible. In this manner, when the lower surface 96 of the coagulation electrode 88 is lightly placed in contact with tissue, the resection electrode 90 remains receded within the coagulation electrode 88 (FIG. 6), so that the coagulation/resection assembly 86 solely effects a tissue coagulation function, whereas when the lower surface 96 of the coagulation electrode 88 is firmly placed in contact with tissue, the leading surface 98 of the resection electrode 90 protrudes from the lower surface 96 of the coagulation electrode 88 into contact with the tissue (FIG. 7), so that the coagulation/resection assembly 86 effects both tissue coagulation and tissue resection functions.

In the illustrated embodiment, the coagulation electrode 88 and resection electrode 90 are in contact with each other and are operated in a monopolar arrangement. In this regard, one or both of the coagulation electrode 88 and resection electrode 90 can be coupled to the electrical connector 32 via the probe shaft 18 (shown in FIG. 1) or wires (not shown). Alternatively, the surface of the resection electrode 90 that would otherwise come in contact with the coagulation electrode 88 can be electrically insulated therefrom, so that the coagulation electrode 88 and resection electrode 90 can be placed within a bipolar arrangement. Alternatively, the resection electrode 90 can be replaced with a blunt resection member that generally takes the same form and shape as the illustrated resection electrode 90, but is not configured to transmit or receive electrical energy.

One method of using the tissue coagulation/resection assembly 86 will now be described in performing a tissue resection. The method comprises absorbing an electrically conductive fluid into the coagulation electrode 88, e.g., by perfusing the coagulation electrode 88 with the electrically conductive fluid via the perfusion port 30 (shown in FIG. 1) and/or dipping the coagulation electrode 88 into the electrically conductive fluid.

Once tissue resection is desired, as illustrated in FIG. 8, the lower surface 96 of the coagulation electrode 88 can be firmly placed in contact with the tissue on opposite lateral sides of the tissue resection line (so that the resection electrode 90 protrudes from the coagulation electrode 88 and contacts the tissue resection line), and electrical energy is conveyed from both the coagulation electrode 88 and resection electrode 90 into the tissue as the tissue coagulation/resection assembly 86 is moved along the resection line. In this manner, the tissue adjacent the resection line is coagulated by the coagulation electrode 88, while the tissue along the resection line is separated by the resection electrode 90. In particular, electrical energy is conveyed from the coagulation electrode 88 through the tissue along the resection line, thereby coagulating a band of tissue that straddles the resection line, and electrical energy is conveyed from the resection electrode 90 through the tissue along the resection line, thereby separating the band of coagulated tissue on the resection line.

If only tissue coagulation is to be achieved, e.g., to precoagulate the tissue along the resection line prior to resection, the lower surface 96 of the coagulation electrode 88 is lightly placed in contact with the tissue (so that the resection electrode 90 remains recessed within the coagulation electrode 88), and electrical energy is conveyed from the coagulation electrode 88 into the tissue as the tissue coagulation/resection assembly 86 is moved along the resection line, as illustrated in FIG. 9. Alternatively, other surfaces of the coagulation electrode 88 can be used to coagulate the tissue. The coagulation electrode 88, while the resection electrode 90 remains recessed, can also be used to stop blood loss at select locations.

Figure 10:
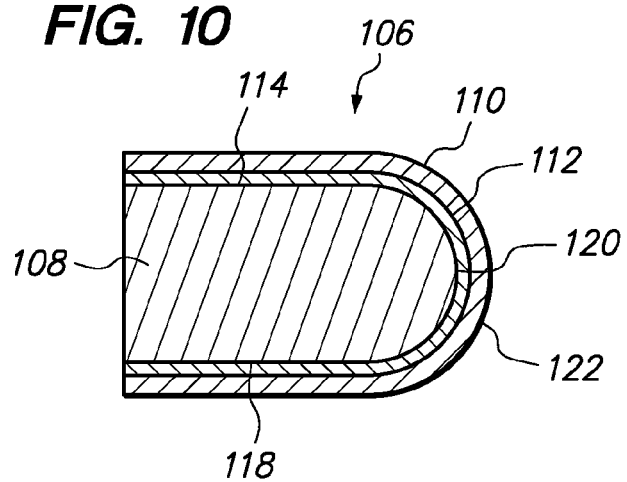
FIG. 10 is a cross-sectional view of still another embodiment of a tissue coagulation/resection assembly that can disposed on the probe used in the tissue coagulation/resection system of FIG. 1.
Figure 11:
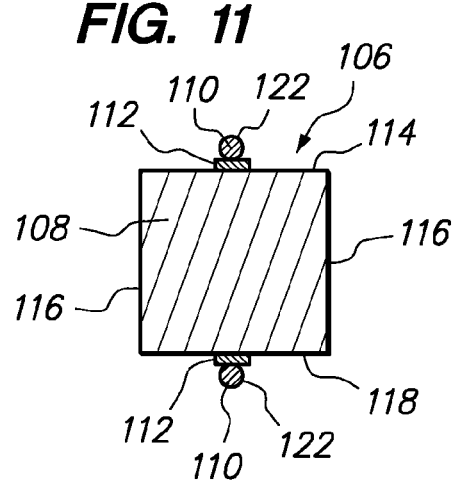
FIG. 11 is a front view of the tissue coagulation/resection assembly of FIG. 10.

Referring to FIGS. 10 and 11, an embodiment of a tissue coagulation/resection assembly 106 constructed in accordance with still another embodiment of the present inventions is described. The coagulation/resection assembly 106 generally comprises a tissue coagulation electrode 108, a tissue resection electrode 110, and a rigid electrical insulating member 112.

The coagulation electrode 108 is composed of a hydrophilic material, which, as previously discussed, is configured for absorbing an electrically conductive fluid, and may be composed of any one of a variety of materials, such as foam. The coagulation electrode 108 may have any one of a variety of shapes, but in the embodiment illustrated in FIG. 11, has a square cross-sectional shape with an upper leading surface 114, opposing lateral leading surfaces 116, and a lower leading surface 118, any of which can be placed in contact with tissue to effect a coagulation function. As illustrated in FIG. 10, the coagulation electrode 108 has a semi-spherical or round distal tip leading surface 120 that can also be placed in contact with tissue to effect a coagulation function. The coagulation electrode 108 may be coupled to the syringe 16 via the perfusion port 30 extending through the probe shaft 18 (shown in FIG. 1).

The tissue resection electrode 110 is composed of a biocompatible and electrically conductive and material, such as stainless steel, gold, platinum, or alloys thereof. The resection electrode 110 has a leading surface 122 that can be placed in contact with tissue to effect a tissue resection function. The electrical insulating member 112 is composed of an electrically insulative material, such as polyether ether ketone (PEEK), polytetrafluoroethylene (PTFE), polyoxymethylene (POM), polyamide, polyamide-imide (PAI), polybutadiene, polycarbonate (PC), or polypropylene (PP). The electrical insulating member 112 is interposed between the resection electrode 110 and the coagulation electrode 108 to electrically isolate the respective electrodes from each other. In particular, the electrical insulating member 112 is suitably mounted to the coagulation electrode 108, e.g., via bonding. Both of the resection electrode 110 and electrical insulating member 112 take the form of a wire or rod looped around the distal tip of the coagulation electrode 108. Either or both of the resection electrode 110 and electrical insulating member 112 is laterally rigid, i.e., has a shear strength, so that the resection electrode 110 resists bending when placed in firm contact with tissue.

The coagulation electrode 108 and resection electrode 110 may be coupled to the electrical connector 32 via the probe shaft 18 (shown in FIG. 1) or wires (not shown). Although electrical energy may be delivered to the coagulation electrode 108 and resection electrode 110 in a monopolar configuration, in the illustrated embodiment, electrical energy is delivered between the coagulation electrode 108 and resection electrode 110 in a bipolar configuration to facilitate tissue resection.

In the bipolar configuration, the coagulation electrode 108 and resection electrode 110 are configured for being simultaneously placed in contact with tissue to be resected. In particular, either the upper surface 114, the lower surface 118, or the distal surface 120 of the coagulation electrode 108 are configured for contacting a surface of tissue to be resected laterally opposite the resection electrode 110. Contact between tissue to be resected and the coagulation electrode 108 is achieved when the resection electrode 110 is firmly placed in contact with the tissue. That is, the leading surface 122 of the resection electrode 110 depresses the tissue to the extent that the upper surface 114, lower surface 118, or distal surface 120 of the coagulation electrode 108 contact the tissue at the periphery of the depression. To ensure that the coagulation electrode 108 and resection electrode 110 can simultaneously contact tissue, the depth or height of the insulating member 112 is small enough, such that the leading surface 122 of the resection electrode 110 is not too offset from the respective leading surface (upper surface 114, lower surface 118, or distal surface 120) of the coagulation electrode 108.

One method of using tissue coagulation/resection assembly 106 will now be described in performing a tissue resection. The method comprises absorbing an electrically conductive fluid into the coagulation electrode 108, e.g., by perfusing the coagulation electrode 108 with the electrically conductive fluid via the perfusion port 30 (shown in FIG. 1) and/or dipping the coagulation electrode 108 into the electrically conductive fluid.

Figure 12:
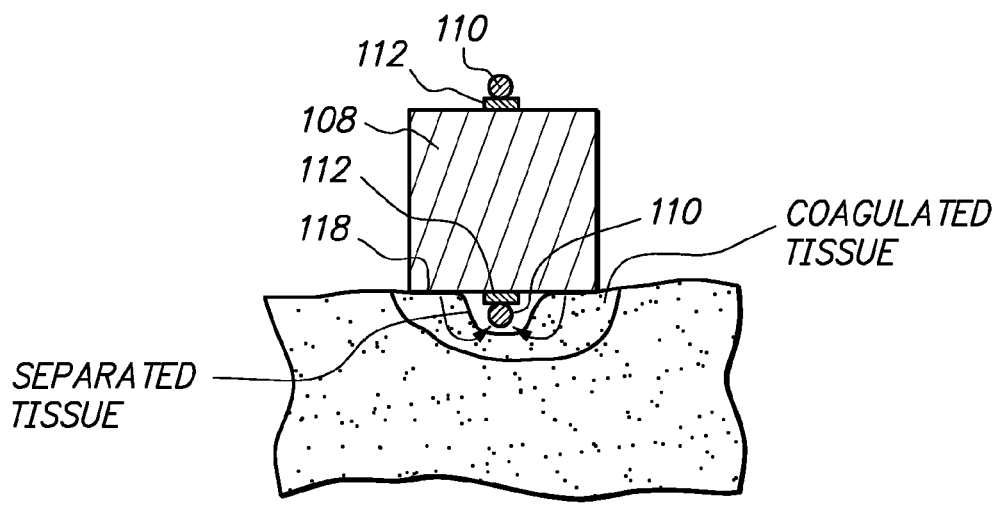
FIG. 12 is a cross-sectional view of the tissue coagulation/resection assembly of FIG. 10, particularly showing the bipolar conveyance of electrical energy to coagulate and separate the tissue.

If tissue resection is desired, as illustrated in FIG. 12, the resection electrode 110 is firmly placed in contact with the tissue along the resection line, so that the upper surface 114, lower surface 118, or distal surface 120 of the coagulation electrode 108 is placed in contact with the tissue on opposite lateral sides of the tissue resection line, and electrical energy is conveyed between the coagulation electrode 108 and resection electrode 110 into the tissue as the tissue coagulation/resection assembly 106 is moved along the resection line. In this manner, tissue adjacent the resection line is coagulated by the coagulation electrode 108, while the tissue along the resection line is separated by the resection electrode 110. In particular, electrical energy (shown by arrows) is conveyed from the coagulation electrode 108 through the tissue along the resection line, and to the resection electrode 110, thereby coagulating a band of tissue that straddles the resection line, and separating the band of coagulated tissue on the resection line.

If only tissue coagulation is to be achieved, e.g., to precoagulate tissue prior to resection, one of the lateral surfaces 116 of the coagulation electrode 108 is placed in contact with the tissue on opposite sides of the resection line, and electrical energy is conveyed from the coagulation electrode 108 into the tissue as the tissue coagulation/resection assembly 106 is moved along the resection line. In this case, the coagulation electrode 108 may be operated in a monopolar mode. The lateral surfaces 116 of the coagulation electrode 108 can also be used to stop blood loss at select locations.

Figure 13:
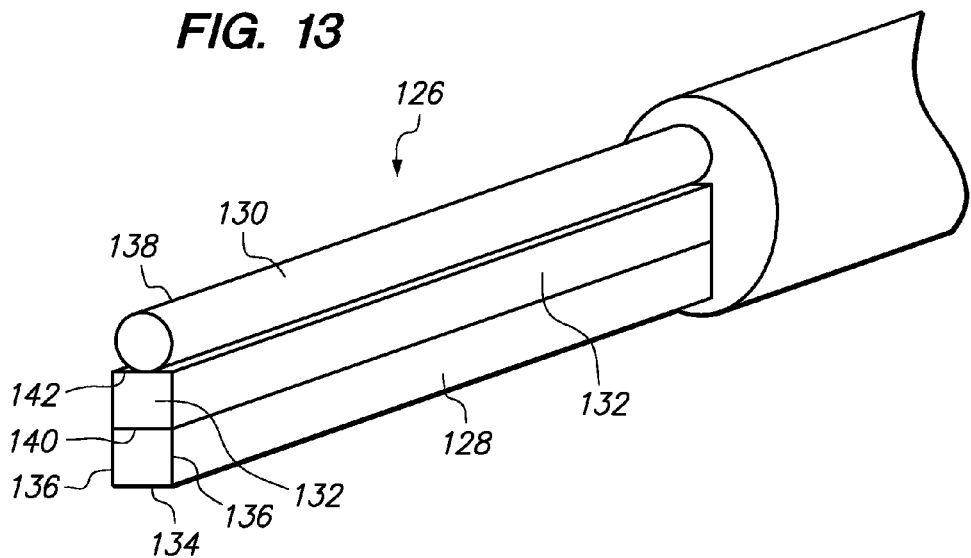
FIG. 13 is a perspective view of yet another embodiment of a tissue coagulation/resection assembly that can disposed on the probe used in the tissue coagulation/resection system of FIG. 1.

Referring to FIG. 13, an embodiment of a tissue coagulation/resection assembly 126 constructed in accordance with yet another embodiment of the present inventions is described. The coagulation/resection assembly 126 generally comprises a tissue coagulation electrode 128, a tissue resection electrode 130, and a rigid electrical insulating member 132.

The coagulation electrode 108 is composed of a hydrophilic material, which, as previously discussed, is configured for absorbing an electrically conductive fluid, and may be composed of any one of a variety of materials, such as foam. The coagulation electrode 108 takes the form of a rod having a rectangular cross-sectional shape with a leading surface 134 that can be placed in contact with tissue to effect a coagulation function. The coagulation electrode 108 also has lateral surfaces 136 that can be placed in contact with cut tissue, as will be described in further detail below. The coagulation electrode 108 may be coupled to the syringe 16 via the perfusion port 30 extending through the probe shaft 18 (shown in FIG. 1). The tissue resection electrode 130 takes the form a wire composed of a biocompatible and electrically conductive and material, such as stainless steel, gold, platinum, or alloys thereof. The resection electrode 130 has a leading surface 138 that can be placed in contact with tissue to effect a tissue resection function, and in particular, a tissue cutting function.

The electrical insulating member 132 is composed of a rigid, electrically insulating, material, such as polyether ether ketone (PEEK), polytetrafluoroethylene (PTFE), polyoxymethylene (POM), polyamide, polyamide-imide (PAI), polybutadiene, polycarbonate (PC), or polypropylene (PP), and takes the form of a rod with a square cross-section and having opposing surfaces 140 and 142. The electrical insulating member 132 is interposed between the coagulation electrode 128 and the resection electrode 130 to electrically isolate the respective electrodes from each other. In particular, the coagulation electrode 128 and resection electrode 130 are suitably mounted to the opposing surfaces 140 and 142 of the insulating member 132, e.g., via bonding. The insulating member 132 is laterally rigid, i.e., has a shear strength, so that the coagulation electrode 128 and resection electrode 130 resist bending when placed in firm contact with tissue.

Figure 14:
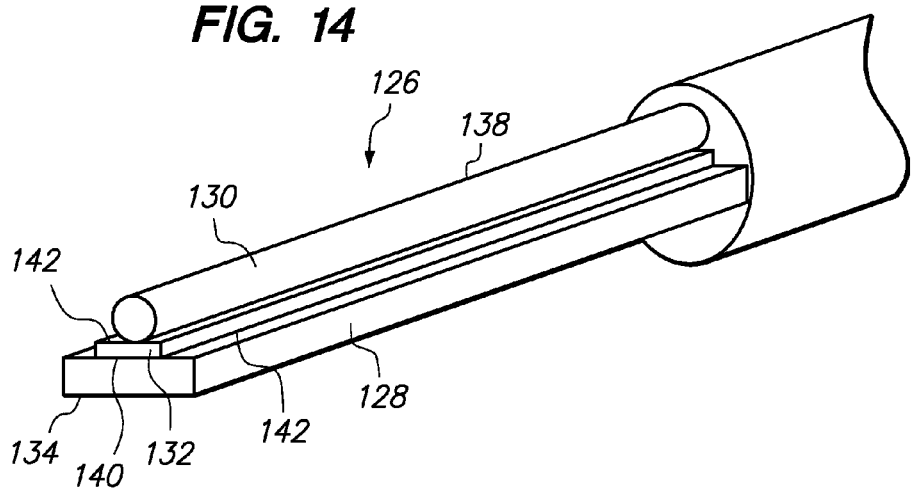
FIG. 14 is a perspective view of a modified tissue coagulation/resection assembly of FIG. 13.

The coagulation electrode 128 and resection electrode 130 may be coupled to the electrical connector 32 via the probe shaft 18 (shown in FIG. 1) or wires (not shown). Although electrical energy may be delivered to the coagulation electrode 128 and resection electrode 130 in a monopolar configuration, in the illustrated embodiment, electrical energy is delivered between the coagulation electrode 128 and resection electrode 130 in a bipolar configuration to facilitate tissue resection. In this case, as illustrated in FIG. 14, the coagulation electrode 128 may be modified to be wider, such that contact between tissue to be resected and the coagulation electrode 128 is achieved when the resection electrode 130 is firmly placed in contact with the tissue. That is, the leading surface 138 of the resection electrode 130 depresses the tissue to the extent that a surface 140 of the coagulation electrode 128 contacts the tissue at the periphery of the depression. To ensure that the coagulation electrode 128 and resection electrode 130 can simultaneously contact tissue, the depth or height of the insulating member 132 is small enough, such that the leading surface 134 of the resection electrode 130 is not too offset from the respective surface 140 of the coagulation electrode 128.

One method of using tissue coagulation/resection assembly 126 will now be described in performing a tissue resection. The method comprises absorbing an electrically conductive fluid into the coagulation electrode 128, e.g., by perfusing the coagulation electrode 128 with the electrically conductive fluid via the perfusion port 30 (shown in FIG. 1) and/or dipping the coagulation electrode 128 into the electrically conductive fluid.

Figure 15:
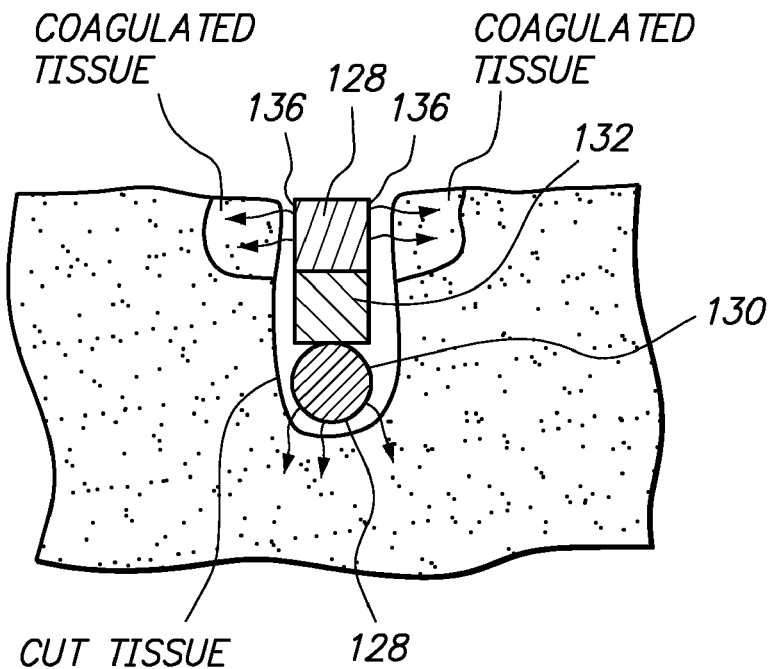
FIG. 15 is a cross-sectional view of the tissue coagulation/resection assembly of FIG. 13, particularly showing the monopolar conveyance of electrical energy to coagulate and separate the tissue.

Using the tissue coagulation/resection assembly 126 of FIG. 13 in a monopolar mode, the leading surface 138 of the resection electrode 130 is placed in contact with the tissue on the resection line, while electrical energy (shown by arrows) is conveyed from the resection electrode 130 into the tissue as the tissue coagulation/resection assembly 126 is moved along the resection line, thereby cutting the tissue along the resection line, as illustrated in FIG. 15. As the resection electrode 130 cuts through the tissue, it obtains a depth that allows the lateral surfaces 136 of the coagulation electrode 128 to contact the tissue on opposite lateral sides of the tissue resection line, thereby coagulating the tissue that has just been cut. In this manner, tissue coagulation and cutting can be accomplished during a single movement of the along the resection line.

Alternatively, rather than cutting the tissue first with the resection electrode 130, the leading surface 134 of the coagulation electrode 128 can be placed in contact with the tissue at opposing lateral sides of the resection line, and electrical energy conveyed from the coagulation electrode 128 into the tissue as the tissue coagulation/resection assembly 126 is moved along the resection line, thereby pre-coagulating the tissue along the resection line prior to resection. The leading surface 138 of the resection electrode 130 can then be placed in contact with the coagulated tissue on the resection line, and electrical energy conveyed from the resection electrode 130 into the tissue as the tissue coagulation/resection assembly 126 is moved along the resection line, thereby cutting the pre-coagulated tissue along the resection line. Tissue coagulation and separation can be repeated until the tissue is completely resected.

Figure 16:
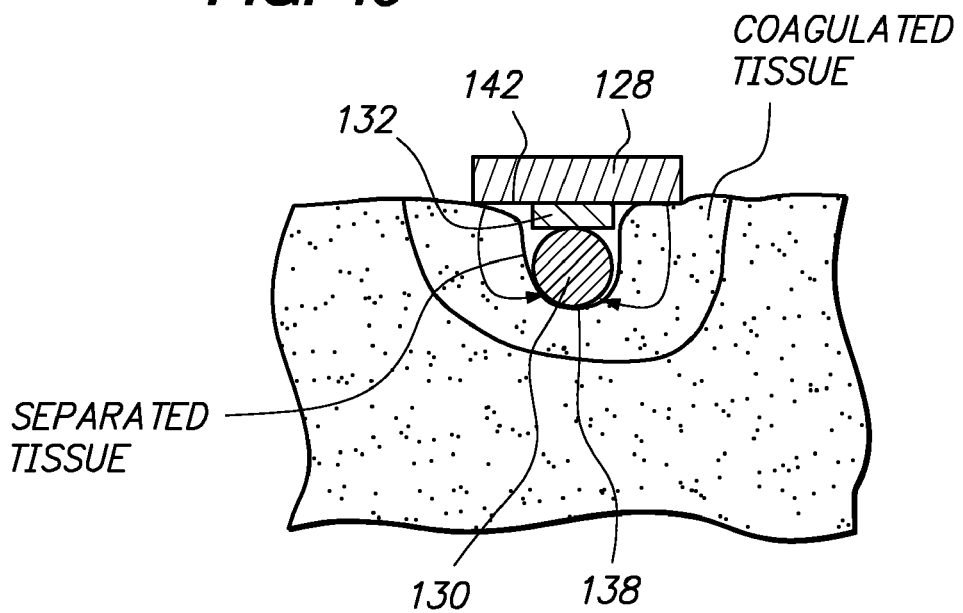
FIG. 16 is a cross-sectional view of the tissue coagulation/resection assembly of FIG. 14, particularly showing the bipolar conveyance of electrical energy to coagulate and separate the tissue.

Using the coagulation/resection assembly 126 of FIG. 14 in a bipolar mode, tissue adjacent the resection line can be coagulated by the coagulation electrode 128, while the tissue along the resection line is separated by the resection electrode 130. In particular, as illustrated in FIG. 16, the leading surface 138 of the resection electrode 130 is firmly placed in contact with the tissue on the resection line, so that the surface 142 of the coagulation electrode 128 is placed in contact with the tissue on opposite sides of the resection line, and electrical energy is conveyed between the coagulation electrode 128 and resection electrode 130 into the tissue as the coagulation/resection assembly 126 is moved along the resection line. In this manner, tissue adjacent the resection line is coagulated by the coagulation electrode 128, while the tissue along the resection line is separated by the resection electrode 130. In particular, electrical energy (shown by arrows) is conveyed from the coagulation electrode 128 through the tissue along the resection line, and to the resection electrode 130, thereby coagulating a band of tissue that straddles the resection line, and separating the band of coagulated tissue on the resection line.

If only tissue coagulation is to be achieved, e.g., to precoagulate tissue prior to resection, the leading surface 134 of coagulation electrode 128 is placed in contact with the tissue on opposite lateral sides of the resection line, and electrical energy is conveyed from the coagulation electrode 128 into the tissue as the tissue coagulation/resection assembly 126 is moved along the resection line. In this case, the coagulation electrode 128 may be operated in a monopolar mode.

Referring to FIGS. 17 and 18, an embodiment of a tissue coagulation/resection assembly 146 constructed in accordance with yet another embodiment of the present inventions is described. The coagulation/resection assembly 146 generally comprises a coagulation electrode 148 and a tissue resection electrode 150.

The coagulation electrode 148 is composed of a hydrophilic material, which, as previously discussed, is configured for absorbing an electrically conductive fluid, and may be composed of any one of a variety of materials, such as foam. In the illustrated embodiment, the coagulation electrode 148 has a tapered circular cross-sectional shape. The coagulation electrode 148 has a lateral surface 152 that can be placed in contact with tissue to effect a tissue coagulation function. The coagulation electrode 148 may be coupled to the syringe 16 via the perfusion port 30 extending through the probe shaft 18 (shown in FIG. 1).

The tissue resection electrode 150 is composed of a biocompatible and electrically conductive and material, such as stainless steel, gold, platinum, or alloys thereof. The resection electrode 150 has a distal tapered electrode tip 154 having a leading surface 156 that can be placed in contact with tissue to effect a tissue resection function. The tissue resection electrode 150 is laterally rigid, i.e., has a shear strength, so that it resists bending when placed in firm contact with tissue. The resection electrode 150 further comprises an annular recess 158 in which the coagulation electrode 148 is suitably mounted, e.g., via bonding. In this regard, the coagulation electrode 148 is located axially proximal to the tapered electrode tip 154. The lateral surface 152 of the tapered coagulation electrode 148 is flush with the leading surface 156 of the tapered electrode tip 154. As illustrated in FIG. 18, the coagulation electrode 148 may be placed in fluid communication with the fluid conduit 28 via a lumen 160 extending through the tissue resection electrode 150 and lateral ports 162.

In the illustrated embodiment, the coagulation electrode 148 and resection electrode 150 are in contact with each other and are operated in a monopolar arrangement. In this regard, one or both of the coagulation electrode 148 and resection electrode 150 can be coupled to the electrical connector 32 via the probe shaft 18 (shown in FIG. 1) or wires (not shown). Alternatively, the surface of the resection electrode 150 that would otherwise come in contact with the coagulation electrode 148 (in this case, the annular recess 158) can be electrically insulated therefrom, so that the coagulation electrode 148 and resection electrode 150 can be placed within a bipolar arrangement. Alternatively, the resection electrode 150 can be replaced with a blunt resection member that generally takes the same form and shape as the illustrated resection electrode 150, but is not configured to transmit or receive electrical energy.

One method of using tissue coagulation/resection assembly 146 will now be described in performing a tissue resection. The method comprises absorbing an electrically conductive fluid into the coagulation electrode 148, e.g., by perfusing the coagulation electrode 148 with the electrically conductive fluid via the perfusion port 30 (shown in FIG. 1) and/or dipping the coagulation electrode 148 into the electrically conductive fluid. The leading surface 156 of the tapered electrode tip 154 is placed in contact with the tissue on the resection line, and the lateral surface 152 of the coagulation electrode 148 is placed in contact with the tissue on opposite lateral sides of the resection line, and electrical energy (shown by arrows) is conveyed from the electrode tip 154 and coagulation electrode 148 into the tissue as the tissue coagulation/resection assembly 146 is moved along the resection line, thereby coagulating tissue along the resection line and cutting the coagulated tissue, as illustrated in FIG. 19. In the optional embodiment where the coagulation electrode 148 and resection electrode 150 are in a bipolar relationship, the electrical energy (shown by arrows) is conveyed from the coagulation electrode 148 to the resection electrode 150, thereby coagulating tissue along the resection line and cutting the coagulated tissue, as illustrated in FIG. 20. In either mode, the axial relationship between the electrode tip 154 and the coagulation electrode 148 allows tissue coagulation and cutting to be accomplished during a single movement along the resection line. Tissue coagulation and separation can be repeated until the tissue is completely resected.

Figure 21:
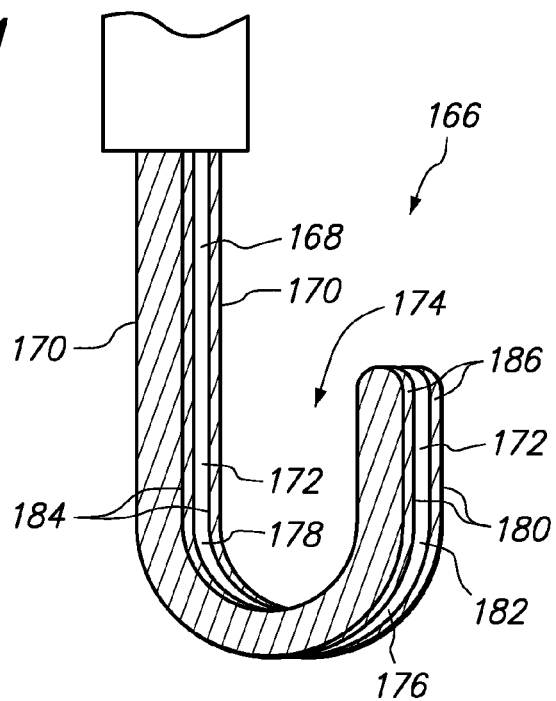
FIG. 21 is a perspective view of yet another embodiment of a tissue coagulation/resection assembly that can disposed on the probe used in the tissue coagulation/resection system of FIG. 1.

Referring to FIG. 21, an embodiment of a tissue coagulation/resection assembly 166 constructed in accordance with yet another embodiment of the present inventions is described. The coagulation/resection assembly 166 generally comprises a blunt tissue dissection member 168 suitably mounted to the distal end of the probe shaft 18 (shown in FIG. 1), and a pair of tissue coagulation electrodes 170 mounted to the dissection member 168.

The dissection member 168 can be composed of any suitable rigid material, but in the illustrated embodiment, is composed of an electrically insulative material, such as polyether ether ketone (PEEK), polytetrafluoroethylene (PTFE), polyoxymethylene (POM), polyamide, polyamide-imide (PAI), polybutadiene, polycarbonate (PC), or polypropylene (PP), to maintain electrical isolation between the coagulation electrodes 170, as will be described in further detail below. In the illustrated embodiment, the dissection member 168 is composed of a unibody structure, although in alternative embodiments, the dissection member 168 may comprise distinct pieces. Any suitable process, such as injection molding, can be used to form the dissection member 168.

The dissection member 168 has a hook-shaped profile, and in particular, includes a pair of opposing rigid member portions 172 that form a channel 174 therebetween where anatomical vessels, such as blood vessels, can be captured, and a distal curved member portion 176 from which the opposing member portions 172 proximal extend. The dissection member 168 has a pair of opposing, flat, inward facing surfaces 178 (only one shown), a pair of opposing, flat, lateral surfaces 180, and a flat, outward facing surface 182.

The coagulation electrodes 170 are composed of a hydrophilic material, which, as previously discussed, is configured for absorbing an electrically conductive fluid, and may be composed of any one of a variety of materials, such as foam. The coagulation electrodes 170 may be coupled to the syringe 16 via the perfusion port 30 extending through the probe shaft 18 (shown in FIG. 1). A plurality of ports (not shown) may be provided within the lateral surfaces 180 of the rigid member portions 172 to facilitate distribution of the electrically conductive fluid within the coagulation electrodes 170 via the dissection member 168. The coagulation electrodes 170 may be coupled to the electrical connector 32 via the probe shaft 18 (shown in FIG. 1) or wires (not shown). Although electrical energy may be delivered to the coagulation electrodes 170 in a monopolar configuration, in the illustrated embodiment, electrical energy is delivered between the coagulation electrodes 170 in a bipolar configuration to facilitate tissue resection.

To this end, the coagulation electrodes 170 are configured for being simultaneously placed in contact with an anatomical vessel, and the coagulation electrodes 170 are configured for being simultaneously placed in contact with tissue to be resected.

Figure 22:
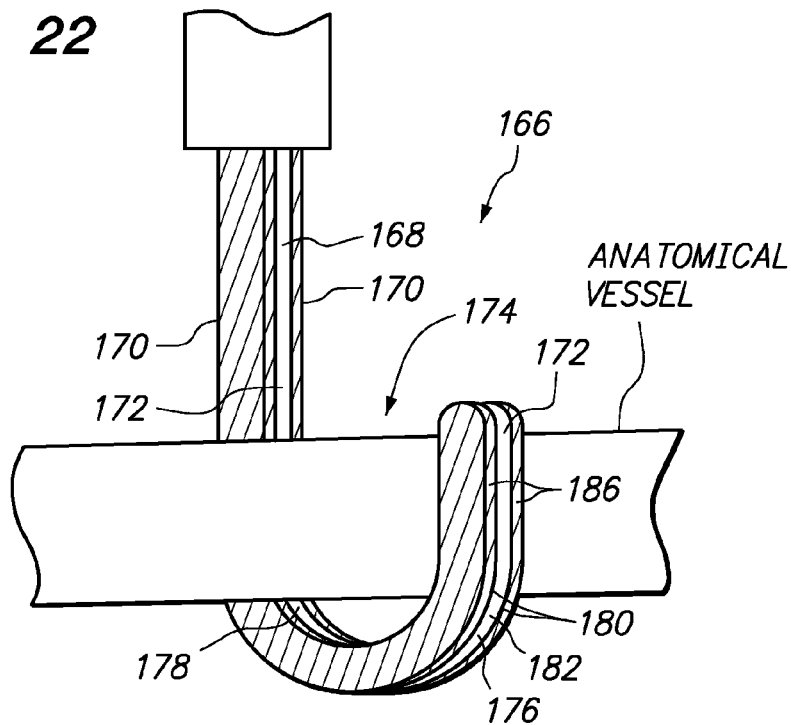
FIG. 22 is a perspective view of the tissue coagulation/resection assembly of FIG. 21, particularly showing an anatomical vessel captured.

In particular, the dissection member 168 is interposed between the coagulation electrodes 170, such that the coagulation electrodes 170 are laterally disposed relative to the dissection member 168. The coagulation electrodes 170 are suitably mounted, e.g., via bonding, to the lateral surfaces 180 of the dissection member 168. In this manner, the coagulation electrodes 170 are configured for contacting the open regions of an anatomical vessel laterally opposite the region of the anatomical vessel closed within the channel 174, with each coagulation electrode 170 having a pair of inward facing leading surfaces 184 (only one shown) configured for contacting opposite sides (i.e., top and bottom) of the anatomical vessel, as illustrated in FIG. 22. Each coagulation electrode 170 also has a pair of outward facing leading surfaces 186 (only one shown) configured for contacting a surface of tissue to be resected laterally opposite of the dissection member 168. In the illustrated embodiment, the inward facing surfaces 184 and outward facing surfaces 186 of the coagulation electrodes 170 are flush with the respective inward facing surfaces 178 and outward facing surfaces 182 of the dissection member 168, although they may be offset therefrom a small amount as long as the coagulation electrodes 170 can simultaneously contact the anatomical vessel to be ligated or the tissue to be resected.

Figure 23A:
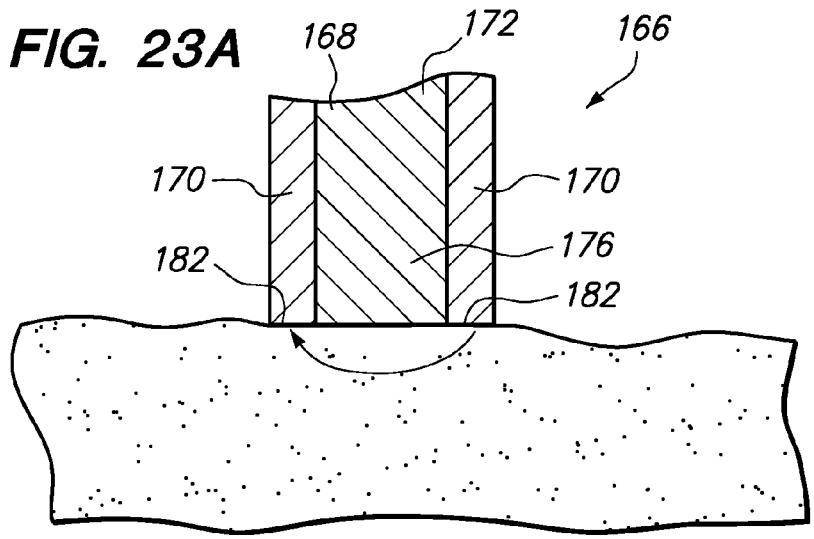
FIG. 23A is a cross-sectional view of the tissue coagulation/resection assembly of FIG. 21, particularly showing the bipolar conveyance of electrical energy through the tissue.
Figure 23B:
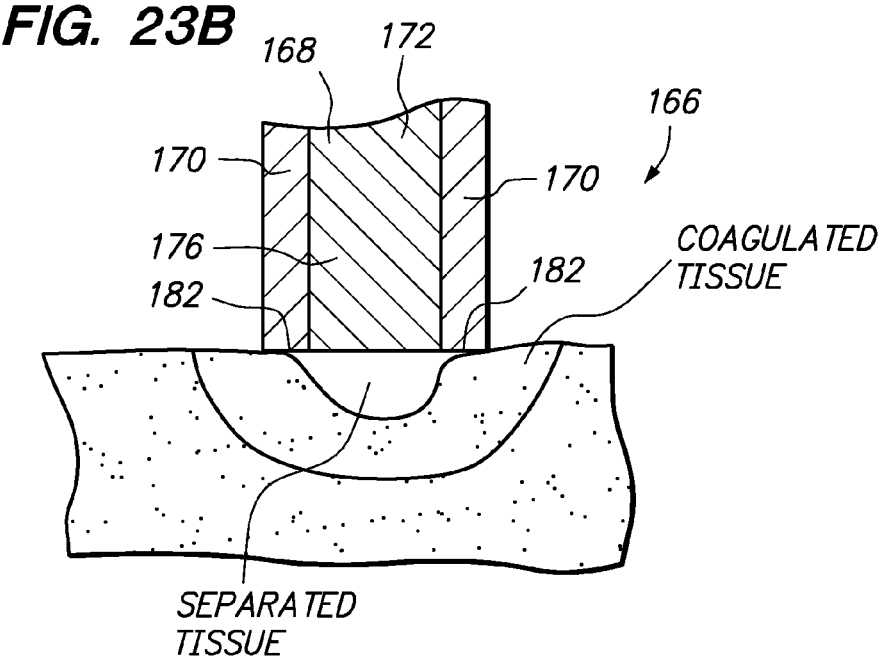
FIG. 23B is a cross-sectional view of the tissue coagulation/resection assembly of FIG. 21, particularly showing the tissue coagulated and separated.

One method of using tissue coagulation/resection assembly 166 will now be described in performing a tissue resection. The method comprises absorbing an electrically conductive fluid into the coagulation electrodes 170, e.g., by perfusing the coagulation electrodes 170 with the electrically conductive fluid via the perfusion port 30 (shown in FIG. 1) and/or dipping the coagulation electrodes 170 into the electrically conductive fluid. The outward facing surface 182 adjacent one of the resection member portions 172 and/or curved member portion 176 is placed in contact with the tissue on the resection line, and the outward facing surfaces 186 of the coagulation electrodes 170 are placed in contact with the tissue on opposite lateral sides of the resection line. Electrical energy is then conveyed between the coagulation electrodes 170 as the tissue coagulation/resection assembly 166 is moved along the tissue resection line. In this manner, tissue adjacent the resection line is coagulated by the coagulation electrodes 170, while the tissue along the resection line is separated by the resection member 168. In particular, as illustrated in FIG. 23A, electrical energy (shown by arrows) is conveyed between the respective coagulation electrodes 170 through the tissue adjacent the resection line. As a result, the electrical energy at the interface between the tissue surface and the outward facing surfaces 182 of the coagulation electrodes 170 coagulates a band of tissue along the resection line, and the mechanical pressure at the interface between the tissue surface and the resection member 168 separates the coagulated band of tissue along the resection line, as illustrated in FIG. 23B.

Alternatively, if the coagulation electrodes 170 are in a monopolar configuration, electrical energy can be conveyed to or from one of the coagulation electrodes 170, while a different portion of that coagulation electrode 170, e.g., a lateral surface of the coagulation electrode 170, is placed on opposite lateral sides of the resection line to coagulate the adjacent tissue. The dissection member 168 can then be used to separate the coagulated tissue along the resection line.

Figure 23C:
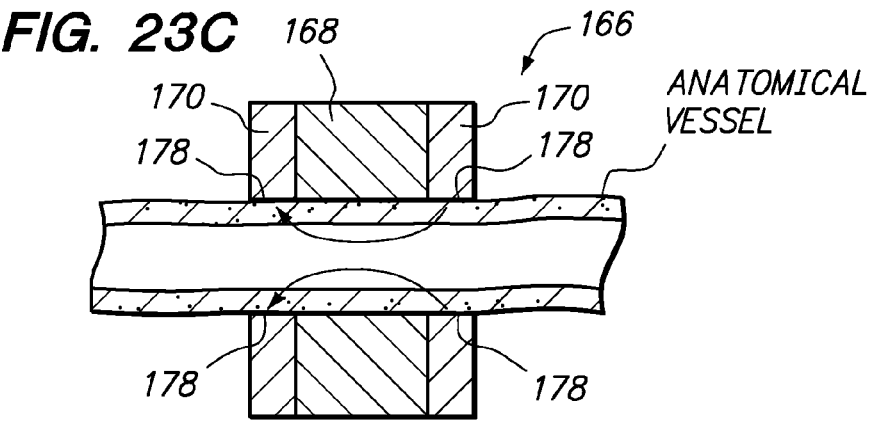
FIG. 23C is a cross-sectional view of the tissue coagulation/resection assembly of FIG. 21, particularly showing an anatomical vessel ligated.

When an anatomical vessel, such as a blood vessel, is encountered, the anatomical vessel can be slid within the channel 174 between the inward facing surfaces 178 of the dissection member 168. Electrical energy is then conveyed between the coagulation electrodes 170 to seal the anatomical vessel. In particular, as illustrated in FIG. 23C, electrical energy (shown by arrows) is conveyed from the respective coagulation electrodes 170 through the vessel tissue. As a result, the electrical energy at the interface between the top side of the vessel and the portions of the coagulation electrodes 170 adjacent one of the member portions 172, and the electrical energy at the interface between the bottom side of the vessel and the portions of the coagulation electrodes 170 adjacent the other of the member portions 172 causes the top and bottom sides of the closed vessel region to seal.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed:

1. A method of resecting a portion of tissue to be removed from a portion of the tissue to be retained within a patient, comprising:

absorbing a volume of an electrically conductive fluid into a hydrophilic electrode, the hydrophilic electrode comprising a porous electrically insulative material, wherein the volume of electrically conductive fluid is sufficient to provide an electrically conductive path through the porous electrically insulative material, wherein the electrically conductive path is broken when the volume of electrically conductive fluid drops below a threshold level;

conveying electrical energy to or from the hydrophilic electrode while being moved in proximity to the tissue along a resection line, whereby tissue adjacent to the resection line is coagulated;

separating the tissue along the resection line to resect the tissue portion to be removed from the tissue portion to be retained;

conveying electrical energy to or from the hydrophilic electrode to seal a blood vessel that traverses the resection line; and transecting the sealed blood vessel.

2. The method of claim 1, wherein the tissue comprises an organ.

3. The method of claim 2, wherein the organ is a liver.

4. The method of claim 1, wherein the tissue to be retained is healthy tissue, and the tissue to be removed is unhealthy tissue.

5. The method of claim 4, wherein the unhealthy tissue is cancerous.

6. The method of claim 1, wherein absorbing the electrically conductive fluid into the hydrophilic electrode comprises dipping the hydrophilic electrode into a source of electrically conductive solution.

7. The method of claim 1, wherein absorbing the electrically conductive fluid into the hydrophilic electrode comprises perfusing the hydrophilic electrode with the electrically conductive fluid under pressure.

8. The method of claim 1, wherein the hydrophilic electrode absorbs an amount of the electrically conductive solution equal to at least the dry weight of the hydrophilic electrode.

9. The method of claim 1, wherein the electrically conductive solution comprises saline.

10. The method of claim 1, wherein the electrical energy is radio frequency (RF) energy.

11. The method of claim 1, wherein the tissue separation comprises electrically separating the tissue along the resection line.

12. The method of claim 11, wherein the hydrophilic electrode electrically separates the tissue.

13. The method of claim 11, wherein another electrode separate from the hydrophilic electrode electrically separates the tissue.

14. The method of claim 13, wherein the hydrophilic electrode and other electrode are mounted on a single probe.

15. The method of claim 14, wherein the electrical energy is conveyed to or from the hydrophilic electrode and the other electrode, wherein tissue coagulation and tissue separation is simultaneously achieved.

16. The method of claim 15, wherein the electrical energy is conveyed between the hydrophilic electrode and the other electrode to simultaneously achieve tissue coagulation and tissue separation.

17. The method of claim 1, wherein the tissue separation comprises mechanically separating the tissue along the resection line.

18. The method of claim 1, wherein the tissue coagulation is performed prior to the tissue separation, whereby the coagulated tissue is separated.

19. The method of claim 1, wherein the sealed blood vessel is transected using at least one electrode.

20. The method of claim 1, wherein the sealed blood vessel is transected using a cutting instrument.

21. The method of claim 1, wherein the blood vessel that traverses the resection line is compressed prior to conveying electrical energy to or from the hydrophilic electrode to seal a blood vessel.

* * * * *